(12) United States Patent
Sueda et al.

(10) Patent No.: US 9,789,037 B2
(45) Date of Patent: *Oct. 17, 2017

(54) ZINC OXIDE PARTICLE, METHOD FOR PRODUCING THE SAME, ULTRAVIOLET SHIELDING AGENT, AND COSMETIC

(71) Applicant: SAKAI CHEMICAL INDUSTRY CO., LTD., Sakai-shi, Osaka (JP)

(72) Inventors: Satoru Sueda, Iwaki (JP); Mitsuo Hashimoto, Iwaki (JP); Mizuho Wada, Sakai (JP)

(73) Assignee: SAKAI CHEMICAL INDUSTRY CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/107,805

(22) PCT Filed: Dec. 25, 2014

(86) PCT No.: PCT/JP2014/084205
§ 371 (c)(1),
(2) Date: Jun. 23, 2016

(87) PCT Pub. No.: WO2015/098992
PCT Pub. Date: Jul. 2, 2015

(65) Prior Publication Data
US 2016/0324742 A1    Nov. 10, 2016

(30) Foreign Application Priority Data
Dec. 27, 2013    (JP) ................................. 2013-271568

(51) Int. Cl.
*A61K 8/02*    (2006.01)
*A61K 8/29*    (2006.01)
(Continued)

(52) U.S. Cl.
CPC .............. *A61K 8/27* (2013.01); *A61K 8/0254* (2013.01); *A61K 8/0262* (2013.01); *A61K 8/29* (2013.01);
(Continued)

(58) Field of Classification Search
None
See application file for complete search history.

(56) References Cited

U.S. PATENT DOCUMENTS 6,660,380 B1 * 12/2003 Ishida ..................... A61K 8/11
427/215

FOREIGN PATENT DOCUMENTS

CN    1884095 A * 12/2006
JP    62-275182 A    11/1987
(Continued)

OTHER PUBLICATIONS

Google English Translation of WO2012147887A1 ([retrieved from on-line website : https://www.google.com/patents/WO2012147887A1?dq=PCT/JP2012/061281&cl=en, last visit Dec. 8, 2016]).*

(Continued)

*Primary Examiner* — Ernst V Arnold
*Assistant Examiner* — Kyung Sook Chang
(74) *Attorney, Agent, or Firm* — Hamre, Schumann, Mueller & Larson, P.C.

(57) ABSTRACT

It is one of the objects of the present disclosure to provide hexagonal plate-shaped zinc oxide particles having suitable performances derived from the shape thereof, that is, zinc oxide particles having improved ultraviolet shielding ratio at the wavelength of 400 nm or less without impairing the direct transition properties of electronic excitation thereof and having remarkably improved ultraviolet shielding ratio for UV-B radiation and UV-A radiation.

(Continued)

A zinc oxide particle containing a solid solution of a Ti element and/or a Fe element and a Zn element in at least a portion thereof, and having a hexagonal plate shape.

7 Claims, 10 Drawing Sheets

(51) Int. Cl.
    *A61K 8/27*     (2006.01)
    *C09C 1/04*     (2006.01)
    *A61Q 17/04*     (2006.01)
    *B05D 3/02*     (2006.01)

(52) U.S. Cl.
    CPC ............... *A61Q 17/04* (2013.01); *B05D 3/02* (2013.01); *C09C 1/04* (2013.01); *C09C 1/043* (2013.01); *A61K 2800/412* (2013.01); *A61K 2800/413* (2013.01); *A61K 2800/621* (2013.01); *C01P 2002/50* (2013.01); *C01P 2002/72* (2013.01); *C01P 2004/04* (2013.01); *C01P 2004/20* (2013.01); *C01P 2004/22* (2013.01); *C01P 2004/64* (2013.01); *C01P 2004/84* (2013.01)

(56) References Cited

FOREIGN PATENT DOCUMENTS

| JP | 63-265819 A | 11/1988 | |
|---|---|---|---|
| JP | 4-26514 A | 1/1992 | |
| JP | 5-70123 A | 3/1993 | |
| JP | 5-222317 A | 8/1993 | |
| JP | 9-188517 A | 7/1997 | |
| JP | 2000-144095 A | 5/2000 | |
| JP | 2002-226826 A | 8/2002 | |
| JP | 2006-306641 A | 11/2006 | |
| JP | WO 2012147887 A1 * | 11/2012 | ............... C01G 9/02 |
| JP | 2013-189369 A | 9/2013 | |
| WO | 03/022954 A1 | 3/2003 | |
| WO | 2012/147886 A1 | 11/2012 | |
| WO | 2012147886 | 11/2012 | |

OTHER PUBLICATIONS

Google English Translation of CN1884095A ([retrieved from on-line website: https://www.google.com/patents/CN1884095A?cl=en, last visit Dec. 8, 2016]).*
"Zinc Oxide Sunscreen & Nanoparticles" ([retrieved from on-line website: https://www.badgerbalm.com/s-33-zinc-oxide-sunscreen-nanoparticles.aspx, last visit Dec. 9, 2016).*
Iron ([retrieved from on-line website: http://www.infoplease.com/encyclopedia/science/iron-natural-occurrence.html, last visit Dec. 9, 2016]).*
Titanium ([retrieved from on-line website: http://www.encyclopedia.com/science-and-technology/chemistry/compounds-and-elements/titanium, last visit Dec. 9, 2016]).*
Xing et al. "Facil Preparation of ZnTiO3 Ceramic Powders in Sodium/Potassium Chloride Melts". J. Am. Ceram. Soc., vol. 89, No. 3, pp. 1150-1152 (2006).
International Search Report for PCT/JP2014/084205, Apr. 7, 2015.

* cited by examiner

Primary particle diameter ($\mu$m) = average value of unidirectional diameters of 250 particles

Fig. 17

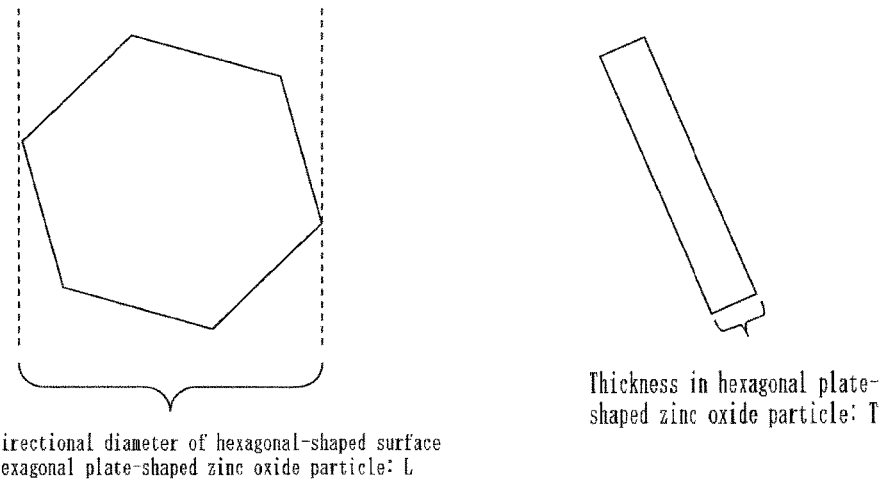

Unidirectional diameter of hexagonal-shaped surface in hexagonal plate-shaped zinc oxide particle: L Thickness in hexagonal plate-shaped zinc oxide particle: T Aspect ratio of hexagonal plate-shaped zinc oxide particles = (average value of unidirectional diameters of hexagonal-shaped surfaces of 250 particles: L)/(average value of thicknesses of 250 particles: T)

Fig. 18

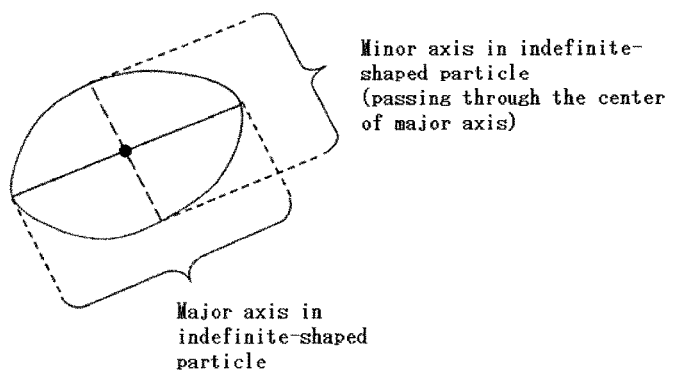

Minor axis in indefinite-shaped particle (passing through the center of major axis)

Major axis in indefinite-shaped particle

Method for measurement of aspect ratio of particles having an indefinite shape: a major axis and a minor axis passing through the center of the major axis of an indefinite-shaped particle in the TEM photograph are measured, and an aspect ratio is determined according to the formula:
Aspect ratio = average value of major axis/minor axis for 250 particles

Fig. 19

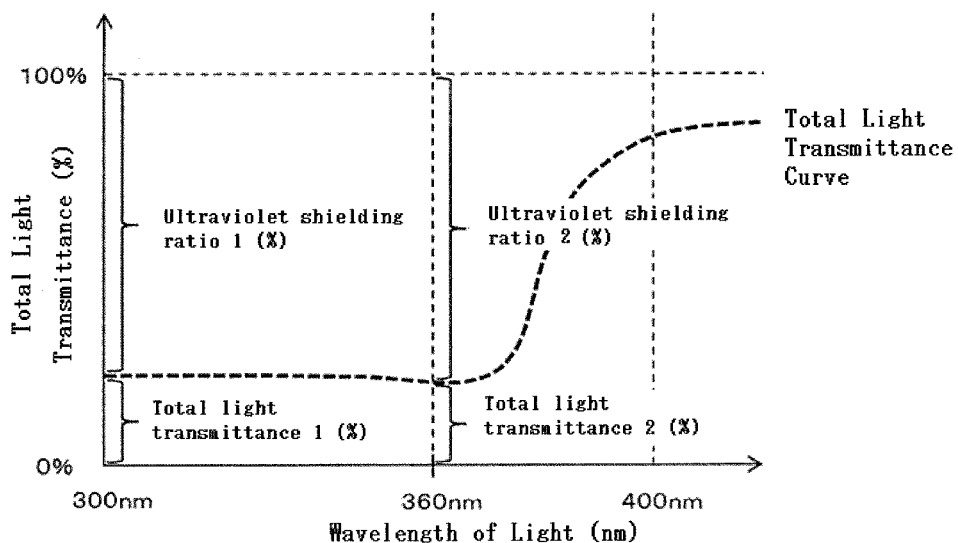

Ultraviolet shielding ratio 1 (%)
= 100(%)-Total light transmittance 1 (%)
Ultraviolet shielding ratio 2 (%)
= 100(%)-Total light transmittance 2 (%)

The larger the value of the ultraviolet shielding ratio 1 (%), the higher the ultraviolet shielding property to UV-B radiation at the wavelength of 300 nm.

The larger the value of the ultraviolet shielding ratio 2 (%), the higher the ultraviolet shielding property to UV-A radiation at the wavelength of 360 nm.

US 9,789,037 B2

ZINC OXIDE PARTICLE, METHOD FOR PRODUCING THE SAME, ULTRAVIOLET SHIELDING AGENT, AND COSMETIC

TECHNICAL FIELD

The present disclosure relates to a zinc oxide particle containing a solid solution represented by $Zn_2TiO_4$ or $ZnFe_2O_4$ in at least a portion thereof, a method for producing the same, an ultraviolet shielding agent, and a cosmetic.

BACKGROUND OF THE DISCLOSURE

An ultraviolet contained in the sunlight is divided into UV-A radiation at 400 to 320 nm, UV-B radiation at 320 to 290 nm, and UV-C radiation at 290 to 100 nm by the wavelength. The UV-A radiation occupies little over than 97% of the total solar ultraviolet amount reaching on the ground, and transmits through a glass or a cloud and permeates to the dermal segment in the back of the skin to cause photoaging such as wrinkle, and slackening.

Conventionally, a responding to UV-B radiation having a strong effect on sunburn has been valued as UV protection. However, further research of photoaging has been done in recent years, and the responding to UV-A radiation captures consumer attention.

For shielding UV-A radiation efficiently, it is needed to combine a large amount of organic ultraviolet absorption agents and/or inorganic ultraviolet shielding agents in products. On the other hand, the organic ultraviolet absorption agent is recognized as a sufficient safety material, but some specific ultraviolet absorption agents are used in limited amounts for cosmetic purpose. From the above, it is needed to shield sufficiently UV-A radiation by using only the inorganic ultraviolet shielding agents.

The inorganic ultraviolet shielding agents such as zinc oxide and titanium oxide to be used in a sunscreen product can reveal the ultraviolet protection performance by the scattering effect of ultraviolet on the powder surface and the effect of absorbing the ultraviolet into the powder particle. The scattering effect depends on the reflection factor of the particle and the particle size, and the absorption effect depends on the band gap energy (Eg) of the powder particle. The Eg of zinc oxide is 3.2 eV and electronic excitation thereof is direct transition so that zinc oxide can absorb effectively the light at the wavelength of 388 nm or less corresponding substantially to the Eg value. On the other hand, rutile type titanium oxide to be widely used in cosmetic use has the Eg of 3.0 eV, but the electronic excitation of titanium oxide is indirect transition so that the light at the wavelength of about 320 nm or less being smaller than 413 nm corresponding to original Eg value can be absorbed effectively.

Further, the Eg of iron oxide (hematite) is 2.2 eV, and the wavelength corresponding to the Eg is 564 nm. Therefore, it is thought that iron oxide absorbs the light at the wavelength of 400 to 564 nm being a visible ray not only the UV-A radiation.

The inventors of the present disclosure completed the invention of hexagonal plate shaped-zinc oxide particle and a method for producing the same (Patent Document 1). The hexagonal plate shaped-zinc oxide particle disclosed in Patent Document 1 has a good smoothness, a soft focus effect, an ultraviolet shielding property, and a visible light transparency, and may be used suitably as an ultraviolet shielding agent for a cosmetic. The zinc oxide particles have more excellent ultraviolet shielding performance than conventional zinc oxide particles, and can be used as an ultraviolet shielding component of a cosmetic. However, it is more preferred to obtain more excellent ultraviolet shielding performance.

An ultraviolet protecting agent composed of titanic acid dizinc fine particles and ultraviolet shielding agent composed of zinc oxide particles in which iron is contained are disclosed in Patent Documents 2 to 5. However, these particles do not have the hexagonal plate shape so that the particles are not particles having the various kinds of performances derived from the above-mentioned hexagonal plate shape.

PRIOR TECHNICAL DOCUMENTS

Patent Documents

[Patent Document 1] WO 2012/147886
[Patent Document 2] Japanese Kokai Publication Sho63-265819
[Patent Document 3] Japanese Kokai Publication Hei9-188517
[Patent Document 4] Japanese Kokai Publication Hei5-222317
[Patent Document 5] Japanese Kokai Publication Sho62-275182

SUMMARY OF INVENTION

Problems to be Solved by the Invention

It is one of the objects of the present disclosure to provide hexagonal plate-shaped zinc oxide particles having suitable performances derived from the shape thereof, that is, zinc oxide particles having improved ultraviolet shielding ratio at the wavelength of 400 nm or less without impairing the direct transition properties of electronic excitation thereof and having remarkably improved ultraviolet shielding ratio for UV-B radiation and UV-A radiation.

Means for Solving Object

The present disclosure relates to a zinc oxide particle containing a solid solution of a Ti element and/or a Fe element and a Zn element in at least a portion thereof, and having a hexagonal plate shape.

The solid solution of a Ti element and/or a Fe element and a Zn element preferably forms a layer covering a surface of the zinc oxide particle as a base material.

The zinc oxide particle preferably contains $Zn_2TiO_4$ or $ZnFe_2O_4$ and has a primary particle diameter of 0.01 μm or more.

In the zinc oxide particle, an amount of a Ti element and/or a Fe element is preferably 5 wt % or more and 30 wt % or less relative to 100 wt % of zinc oxide particle in terms of $TiO_2$ and/or $Fe_2O_3$.

The present disclosure relates to a method for producing the zinc oxide particle comprising a step (1-1) of adding an aqueous solution of a titanium salt and/or an iron salt and an alkaline aqueous solution to a water-based slurry of raw zinc oxide particles having a hexagonal plate shape at a temperature of 10° C. to 90° C. while keeping a pH at 9±3, and a step (1-2) of baking the coated zinc oxide particle obtained in the step (1-1).

The present disclosure relates to a method for producing the zinc oxide particle comprising a step (2-1) of adding raw zinc oxide particles to an aqueous solution of a zinc salt obtained by dissolving a titanium salt and/or an iron salt and heat aging the raw zinc oxide particles, and a step (2-2) of baking the titanium hydroxide-containing zinc oxide particle and/or iron hydroxide-containing zinc oxide particle obtained in the step (2-1).

The present disclosure relates to a zinc oxide particle obtained by the method.

The present disclosure relates to an ultraviolet shielding agent comprising the zinc oxide particle.

The present disclosure relates to a cosmetic comprising the zinc oxide particle.

Effects of the Invention

The zinc oxide particle of the present disclosure is a particle having an improved ultraviolet shielding ratio at the wavelength of 400 nm or less without impairing the direct transition properties of electronic excitation of hexagonal plate-shaped zinc oxide and having remarkably improved ultraviolet shielding ratio for UV-B radiation and UV-A radiation.

BRIEF DESCRIPTION OF THE DRAWINGS

FIG. 17 is a schematic view illustrating a method for measuring an aspect ratio of hexagonal plate-shaped zinc oxide particles.

FIG. 18 is a schematic view illustrating a method for measuring an aspect ratio of indefinite-shaped zinc oxide particles.

FIG. 19 is an explanation view of ultraviolet shielding ratio 1(%) and ultraviolet shielding ratio 2(%).

DETAILED DESCRIPTION OF PREFERRED EMBODIMENTS

Figure 1:
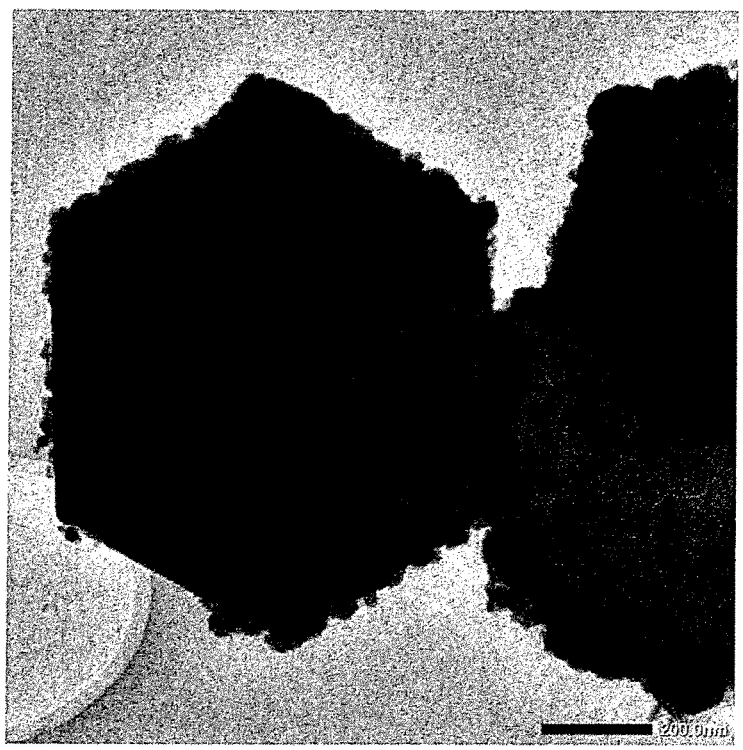
FIG. 1 is a transmission electron microscope photograph of $Zn_2TiO_4$-coated zinc oxide particles obtained in example 1.

The present disclosure will be described in detail hereinafter.

The present disclosure relates to a zinc oxide particle containing a solid solution of a Ti element and/or a Fe element and a Zn element in at least a portion thereof, and having a hexagonal plate shape. That is, as for the zinc oxide particle having an excellent performance as disclosed in Patent Document 1, the ultraviolet absorption performance thereof can be changed to obtain zinc oxide particles having a more improved ultraviolet shielding performance by containing a solid solution of a Ti element and/or a Fe element and a Zn element in at least a portion thereof. The zinc oxide particle of the present disclosure is new zinc oxide particle, which is covered by the solid solution or which contains the solid solution inside, having the direct transition performance of electronic excitation of zinc oxide and the ultraviolet shielding performance of $Zn_2TiO_4$ or $ZnFe_2O_4$.

(Solid Solution of Ti Element and/or Fe Element and Zn Element)

The zinc oxide particle of the present disclosure contains a solid solution of a Ti element and/or a Fe element and a Zn element in at least a portion thereof. That is, the zinc oxide particle contains $Zn_2TiO_4$ and/or $ZnFe_2O_4$ in at least a portion thereof, and may be one of which the surface is covered by these compounds or one in which a part consisting of $Zn_2TiO_4$ and/or $ZnFe_2O_4$ exist partially. Zinc oxide particle of which the surface is covered by $Zn_2TiO_4$ and/or $ZnFe_2O_4$ is preferred because the visible light transmittance thereof is high so that more improved transmittance can be achieved when contained in a cosmetic.

The zinc oxide particle of the present disclosure may contain both of a Ti element and a Fe element. An amount of a Ti element and/or a Fe element is preferably 5 wt % or more and 30 wt % or less relative to 100 wt % of zinc oxide particle in terms of $TiO_2$ and/or $Fe_2O_3$, and more preferably 7 wt % or more and 25 wt % or less. When less than 5 wt %, it is not preferred because the ultraviolet absorption performance at the wavelength of 400 nm or less cannot be efficiently obtained. When over 30 wt %, it is not preferred because the direct transition property of electronic excitation of the zinc oxide particle is loosed. The amount relative to zinc oxide particle in terms of $TiO_2$ and/or $Fe_2O_3$ is a value measured using a X-ray fluorescence analyzer ZSX Primus II (manufactured by Rigaku Corporation), and the used software is EZ scan (SQX).

In the present disclosure, the Ti element and/or Fe element forms a solid solution with a Zn element. It is more preferred that the solid solution exists inside the zinc oxide particle or on the surface thereof in a state represented by a general formula $Zn_2TiO_4$, or $ZnFe_2O_4$.

The formation of the solid solution represented by $Zn_2TiO_4$ and/or $ZnFe_2O_4$ can be confirmed by X-ray diffraction. As described in detail in example, the zinc oxide particle of the present disclosure is measured by X-ray diffraction, then the diffraction spectra derived from ZnO and $Zn_2TiO_4$ and/or $ZnFe_2O_4$ can be observed. Thereby, it can be confirmed that the Ti element and/or Fe element exist in a state of solid solution as mentioned above. The X-ray diffraction is measured using an X-ray diffractometer Ultima III (manufactured by Rigaku Corporation) having an X-ray tube with copper.

The zinc oxide particle of the present disclosure is preferably has higher ultraviolet shielding ratio than a raw zinc oxide particle to be matrix when the solid solution represented by $Zn_2TiO_4$ or $ZnFe_2O_4$ is formed by covering the hexagonal plate-shaped raw zinc oxide particle to be matrix. The ultraviolet comprises UV-A radiation and UV-B radiation, and it is preferred that the coated zinc oxide particle has a higher ultraviolet shielding ratio for one or both of the above-mentioned radiations than the raw zinc oxide particle to be matrix. Specifically, the ratio of (ultraviolet shielding ratio of the coated zinc oxide particle (%)/(ultraviolet shielding ratio of the raw zinc oxide particle which is the matrix of the coated zinc oxide particle (%)) is preferably 1.1 or more.

In the specification, the ultraviolet shielding ratio is a value calculated based on the total light transmittance measured according to the following conditions as to a coating film which is prepared by the method described in example.
(Total Light Transmittance 1, Total Light Transmittance 2)

In the specification, the total light transmittance 1(%) and total light transmittance 2(%) are values determined by measuring a prepared coating film with the use of a spectrophotometer V-570 (manufactured by JASCO Corporation). The total light transmittance 1(%) is a value of total light transmittance at the wavelength of 300 nm, and the total light transmittance 2(%) is a value of total light transmittance at the wavelength of 360 nm. The smaller the total light transmittance 1(%), the higher the ultraviolet shielding effect to the ultraviolet in UV-B radiation, and the smaller the total light transmittance 2(%), the higher the ultraviolet shielding effect to the ultraviolet in UV-A radiation.
(Ultraviolet Shielding Ratio 1, Ultraviolet Shielding Ratio 2)

In the specification, the ultraviolet shielding ratio is calculated according to the following formulas using the above-mentioned total light transmittance.

Ultraviolet shielding ratio 1(%)=100%−the total light transmittance 1(%)

Ultraviolet shielding ratio 2(%)=100%−the total light transmittance 2(%)

That is, the value of the ultraviolet shielding ratio 1(%) means a shielding ratio to the ultraviolet at the wavelength of 300 nm, and the larger this value, the higher the ultraviolet shielding property to UV-B radiation.
The value of the ultraviolet shielding ratio 2(%) means a shielding ratio to the ultraviolet at the wavelength of 360 nm, and the larger this value, the higher the ultraviolet shielding property to UV-A radiation.
An explanation drawing 19 is attached to make it easy to understand relationships between the total light transmittance 1(%), the total light transmittance 2(%), the ultralight shielding ratio 1(%), and the ultralight shielding ratio 2(%).

(The Ratio of (Ultraviolet Shielding Ratio 1 of Coating Film Containing the Coated Zinc Oxide Particle (%)/(Ultraviolet Shielding Ratio 1 of Coating Film Containing the Raw Zinc Oxide Particle which is the Matrix of the Coated Zinc Oxide Particle (%)))

In the zinc oxide particle of the present disclosure, when the solid solution represented by $Zn_2TiO_4$ and/or $ZnFe_2O_4$ is formed by covering, the ratio of (ultraviolet shielding ratio 1 of a coating film containing the coated zinc oxide particle (%)/(ultraviolet shielding ratio 1 of a coating film containing the raw zinc oxide particle which is the matrix of the coated zinc oxide particle (%)) for UV-B radiation is preferably 1.1 or more.

(The Ratio of (Ultraviolet Shielding Ratio 2 of Coating Film Containing the Coated Zinc Oxide Particle (%)/(Ultraviolet Shielding Ratio 2 of Coating Film Containing the Raw Zinc Oxide Particle which is the Matrix of the Coated Zinc Oxide Particle (%)))

In the zinc oxide particle of the present disclosure, when the solid solution represented by $Zn_2TiO_4$ and/or $ZnFe_2O_4$ is formed by covering, the ratio of (ultraviolet shielding ratio 2 of a coating film containing the coated zinc oxide particle (%)/(ultraviolet shielding ratio 2 of a coating film containing the raw zinc oxide particle which is the matrix of the coated zinc oxide particle (%)) for UV-A radiation is preferably 1.1 or more.
(Shape of Zinc Oxide Particle)

The zinc oxide particle of the present disclosure has a hexagonal plate shape. Concerning the zinc oxide particle having such shape, a superior ultraviolet shielding performance can be shown and further an excellent function can be expressed as a component for a cosmetic by the physical effect derived from the specific particle shape as disclosed in Patent Document 1. More specifically, the zinc oxide particle have a smooth feeling derived from the hexagonal plate shape, and a superior soft focus property. The zinc oxide particle of the present disclosure is the hexagonal plate-shaped zinc oxide particle having such excellent effects so that the zinc oxide particle has more improved ultraviolet absorption ability in the region of 400 nm or less.

The zinc oxide particle having a hexagonal plate shape is not particularly limited but it is preferably one as described later in detail.

The zinc oxide particles of the present disclosure preferably have a primary particle diameter of 0.01 μm or more. By appropriately controlling the primary particle diameter of the zinc oxide particles, various kinds of performance such as a proper slippage, a soft focus effect, an ultraviolet shielding property, and a transparency to visible light can be selectively imparted. The primary particle diameter is more preferably 0.02 μm or more, and still more preferably 0.03 μm or more.

The upper limit of the primary particle diameter is not particularly limited but preferably 100 μm, more preferably 50 μm, and still more preferably 25 μm.

Figure 16:
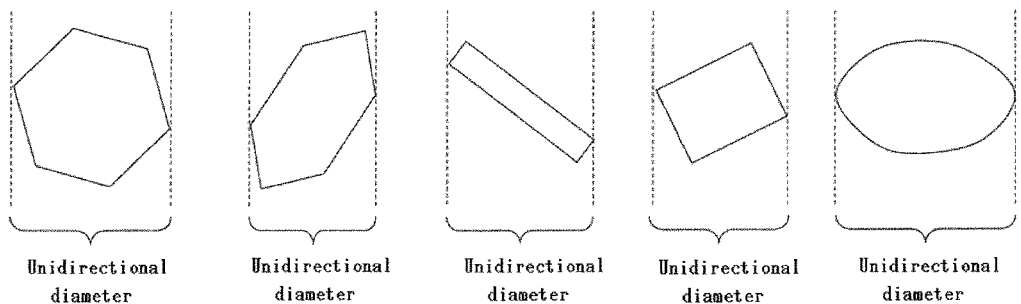
FIG. 16 is a schematic view illustrating a method for measuring a primary particle diameter of zinc oxide particles in examples and comparative examples.

In the specification, the primary particle diameter is a particle diameter (μm) defined by a unidirectional diameter in a visual field of 2000 to 50000 magnification in a transmission electron microscope JEM-2100 (manufactured by JEOL Ltd.) photograph (distance between two parallel lines in a fixed direction with a particle held therebetween; measurements are made in a fixed direction regardless of shapes of particles on the image), and is obtained by measuring the unidirectional diameters of 250 primary particles in the TEM photograph and determining an average value of a cumulative distribution thereof. FIG. 16 is attached for illustrating the measurement method of the primary particle diameter.

The aspect ratio of the hexagonal plate-shaped zinc oxide particles of the present disclosure is preferably 2.5 or more. That is, the hexagonal plate-shaped zinc oxide particles are zinc oxide particles having hexagonal plate shape, and particularly when they are used for a cosmetic, good slippage and excellent comfort in use can be achieved owing to the above-mentioned shape. In the present disclosure, the aspect ratio of hexagonal plate-shaped zinc oxide particle is a value determined as a ratio of L/T where L is an average value of measured particle diameters (μm) of 250 particles, the particle diameter defined by a unidirectional diameter for particles in which the hexagonal-shaped surface of the hexagonal plate-shaped zinc oxide particle faces frontward (distance between two parallel lines in a fixed direction with a particle held therebetween; measurements are made in a fixed direction for particles in which the hexagonal-shaped surface on the image faces frontward), and T is an average value of measured thicknesses (μm) (length of the shorter side of rectangle) of 250 particles for particles in which the side surface of the hexagonal plate-shaped zinc oxide particle faces frontward (particles that appear rectangular), in a visual field of 2000 to 50000 magnification in a transmission electron microscope JEM-2100 (manufactured by JEOL Ltd.) photograph. For the method for measurement of an aspect ratio, FIG. 17 is attached. The aspect ratio is more preferably 2.7 or more, and still more preferably 3.0 or more.

For the aspect ratio of the particles having an indefinite particle shape in comparative examples of the specification, major axis of each of 250 indefinite-shaped zinc oxide particles and minor axis passing through the center of the major axis are measured in a visual field of 2000 to 50000 magnification in a transmission electron microscope JEM-2100 (manufactured by JEOL Ltd.) photograph, and a ratio between the lengths of the major axis and the minor axis: major axis/minor axis is determined. Then, an average value of a cumulative distribution thereof is determined as an aspect ratio. The method for measurement of an aspect ratio of the indefinite-shaped zinc oxide particles is shown in FIG. 18.

(Production Method)

A method for producing the zinc oxide particle of the present disclosure is not particularly limited but includes a method of treating the raw zinc oxide particle obtained according to the method of Patent Document 1 with a compound containing Fe and/or Ti, a method for performing a reaction of the production method of the hexagonal plate-shaped zinc oxide particle disclosed in Patent Document 1 (method for producing zinc oxide comprising a step of aging fine zinc oxide particle in an aqueous solution of zinc salt) in the presence of Fe ion and/or titanium ion, for example.

More specifically, the method is especially preferably one of the following methods:
a production method comprising a step (1-1) of adding an aqueous solution of a titanium salt and/or iron salt and an alkaline aqueous solution to a water-based slurry of raw zinc oxide particles being hexagonal plate-shaped while maintaining the pH and temperature conditions and a step (1-2) of baking the coated zinc oxide particles obtained in the step (1-1) (production method 1), and
a production method comprising a step (2-1) of adding the zinc oxide particles to an aqueous solution of zinc salt obtained by dissolving a titanium salt and/or an iron salt and heat aging the mixture, and a step (2-2) of baking the hydroxide-containing hexagonal plate-shaped zinc oxide particle obtained in the step (2-1) (production method 2).

(Production Method 1)

The production method comprises steps of adding the raw zinc oxide particle having a hexagonal plate shape to a liquid medium to prepare a water-based slurry, forming a surface coating by precipitating a titanium salt and/or iron salt on the surface of the raw zinc oxide particle in the water-based slurry, and baking to obtain a coating. The X-ray analysis of the coated zinc oxide particle obtained by this production method has revealed that the coating of solid solution consisting of a Ti element and/or a Fe element and a Zn element not a coating of titanium oxide and/or iron oxide is formed.

As the hexagonal plate-shaped zinc oxide particle which are used in the above-mentioned step as the raw zinc oxide particle, the particles obtained by the production method disclosed in Patent Document 1 are preferably used.

The production method of zinc oxide particle disclosed in Patent Document 1 comprises a reaction in a slurry. After the completion of the reaction, the obtained particles may be subjected to the production method of the present disclosure, or may be subjected to a step such as filtration, water washing, drying and baking, and next dispersed in an aqueous medium to make water-based slurry, again.

A concentration of the raw zinc oxide particles having a hexagonal plate shape is preferably 10 to 500 g/l in the slurry.

The liquid medium composing the slurry is preferably water or a mixed liquid of water and a water-soluble organic solvent, and most preferably water. When the mixed liquid of water and a water-soluble organic solvent is used, solvents which can be mixed with water at an arbitrary ratio as the water-soluble organic solvent can be used, for example lower alcohols including methanol and ethanol, and acetone. An amount of the water-soluble organic solvent to be used is preferably 1 to 30 wt % relative to the total amount of the mixed solvent.

A dispersant may be used according to need on the preparation of the slurry.

The titanium salt is not particularly limited but includes titanium sulfate, titanium tetraalkoxide such as titanium tetraisopropoxide, and titanium tetrachloride, for example.

The iron salt is not particularly limited but includes ferrous acetate, triacetic acid iron, ferrous chloride, ferric chloride, ferrous sulfate, ferric sulfate, ferrous nitrate, and ferric nitrate, for example.

A concentration of the titanium salt and/or iron salt in the aqueous solution of titanium salt and/or iron salt is preferably 50 to 300 g/l. It is preferred to use the aqueous solution with the above-mentioned concentration range because a uniform covering layer can be formed on the surface of the raw zinc oxide particles to be matrix without reducing the productivity.

A component other than the titanium salt and/or iron salt and water is not needed in the aqueous solution of the titanium salt and/or iron salt, but may be compounded such that the effect of the present disclosure is not affected.

An alkaline compound in the alkaline aqueous solution is not particularly limited but may include sodium hydroxide, potassium hydroxide, ammonia and so on. A concentration of the alkaline aqueous solution is not particularly limited but may be 5 to 30 wt %, for example.

In the step (1-1), the aqueous solution of the titanium salt and/or iron salt and the alkaline aqueous solution are added while maintaining the pH and temperature conditions. By doing this step, the titanium and/or iron are precipitated uniformly to achieve the purpose suitably.

When the aqueous solution of titanium salt and/or iron salt and the alkaline aqueous solution are added, the conditions of pH and temperature are preferably that pH is 9±3 and temperature is 10° C. to 90° C. A reaction time is not particularly limited but may be 10 to 360 minutes.

The aqueous solution of titanium salt and/or iron salt and the alkaline aqueous solution are preferably added simultaneously onto the different positions of the slurry surface which is the target of the adding. Titanium hydroxide particles having uniform shape and uniform particle diameter and/or iron hydroxide particles having uniform shape and uniform particle diameter may be deposited to cover the surface of the zinc oxide particles to be matrix by adding them at the same time. A method for adding is not particularly limited but includes a method of adding a constant amount continuously by a pump. The adding amount of the aqueous solution is preferably an amount corresponding to the titanium and/or iron amount in the zinc oxide particle to be desired. In the case of adding the aqueous solution of titanium salt and/or iron salt and the alkaline aqueous solution simultaneously to the slurry, the slurry is preferably stirred. By doing this, a uniform layer of titanium hydroxide particle and/or iron hydroxide particle can be formed on the surface of the zinc oxide particle. The slurry may be stirred by a usual method, for example, a method using a stirrer and so on.

The slurry obtained by the above-mentioned step (1-1) may be subjected to a step of filtering, and water washing and drying if necessary, then hydroxide-coated zinc oxide particles can be obtained. The obtained hydroxide-coated zinc oxide particles are baked in the step (1-2). By doing this, a solid solution composed of Ti elements and/or Fe element and Zn element may be formed.

In the step (1-2), the baking temperature is preferably 400 to 900° C. It is preferred that the temperature is 500° C. or more because the crystallinity and the ultraviolet shielding effect of the particles can be improved. The baking atmosphere in the step (1-2), is not particularly limited but includes air, oxygen, nitrogen, carbon dioxide, hydrogen, argon, and methane. The baking time is preferably 1 to 50 hours, although it depends on the baking temperature.

(Production Method 2)

The production method 2 comprises a step (2-1) of heat aging raw zinc oxide particles in an aqueous solution of zinc salt obtained by dissolving a titanium salt and/or an iron salt.

The titanium salt and/or iron salt which can be used in the step (2-1) may include the above-mentioned compounds. The zinc salt is not particularly limited but includes zinc sulfate, zinc nitrate, zinc acetate, zinc chloride, zinc formate and so on.

A concentration of the zinc salt in the aqueous solution of zinc salt is preferably 0.005 to 4.0 mol/l. The concentration of titanium salt and/or iron salt in the aqueous solution of zinc salt is preferably 50 to 300 g/l.

The liquid medium composing the aqueous solution of zinc salt is preferably water or a mixed liquid of water and a water-soluble organic solvent, and most preferably water. When the mixed liquid of water and a water-soluble organic solvent is used, solvents which can be mixed with water at an arbitrary ratio as the water-soluble organic solvent can be used, for example lower alcohols including methanol and ethanol, and acetone. The amount of the water-soluble organic solvent to be used is preferably 1 to 30 wt % relative to the total amount of the mixed solvent.

A dispersant may be added according to need, when the slurry is prepared.

The shape of the raw zinc oxide particle in the production method 2 is not limited to a hexagonal plate shape, and zinc oxide particles having any shapes may be used.

The raw zinc oxide particles are added to the aqueous solution of zinc salt, stirred and dispersed to obtain a slurry. The reaction may be done in the slurry.

A concentration of the raw zinc oxide particle is preferably 10 to 500 g/l relative to the total amount of the slurry. A reaction temperature is preferably 10 to 110° C., and a reaction time is preferably 0.5 to 24 hours. A pH of the slurry on performing the step (2-1) is preferably 5.5 to 13.5.

The slurry obtained by the above-mentioned step (2-1) may be subjected to a step of filtering, and water washing and drying if necessary, then hydroxide-containing zinc oxide particles can be obtained. The obtained hydroxide-containing zinc oxide particles are baked in the step (2-2). By doing this, a solid solution composed of a Ti element and/or a Fe element and a Zn element may be formed.

In the step (2-2), the baking temperature is preferably 400 to 900° C. It is preferred that the temperature is 500° C. or more because the crystallinity and the ultraviolet shielding effect of the particles can be improved. The baking atmosphere in the step (2-2), is not particularly limited but includes air, oxygen, nitrogen, carbon dioxide, hydrogen, argon, and methane. The baking time is preferably 1 to 5 hours, although it depends on the baking temperature.

(Surface Treatment)

The zinc oxide particle of the present disclosure may be subjected to a surface treatment. The surface treatment is not particularly limited but includes a surface treatment to form a layer of at least one compound selected from the group consisting of silicon oxides, hydrates of silicon oxide, aluminum oxides, and aluminum hydroxides, a surface treatment using a water-repellent organic compound, and a surface treatment using a coupling agent such as silane coupling agents and titanium coupling agents. These surface treatments may be used in combination.

The formation of a layer using at least one compound selected from the group consisting of silicon oxides, hydrates of silicon oxide, aluminum oxides, and aluminum hydroxides may be done by a method of depositing a Si source compound and/or Al source compound on a powder surface through hydrolysis or thermolysis. The Si source compound and/or Al source compound include compounds which can easily convert to $SiO_2$, $Al(OH)_3$, or $Al_2O_3$ such as tetraalkoxysilane and hydrolysis condensate thereof, sodium silicate, potassium silicate, aluminum alkoxide and hydrolysis condensate thereof, and sodium aluminate.

The hydrolysis reaction is not particularly limited but a method using an acid such as sulfuric acid, hydrochloric acid, acetic acid, and nitric acid may be used. A neutralizing method in the treatment method using the water dispersion may be any one of a method of adding the Si source compound and/or Al source compound after adding the acid to the dispersion, a method of adding the acid after adding the Si source compound and/or Al source compound to the dispersion, and a method of adding the acid and the Si source compound and/or Al source compound at the same time to the dispersion.

The treatment with the water repellent organic compound is not particularly limited but includes a treatment using silicone oils, alkylsilanes, alkyltitanates, alkylaluminates, polyolefins, polyesters, metal soaps, amino acids, or amino acid salts. Among them, silicone oils are preferred because of good chemical stability. The specific example of the silicone oil includes dimethylpolysiloxane (for example, KF-96A-100cs manufactured by Shin-Etsu Chemical Co., Ltd., DM10 manufactured by wacker asahikasei silicone co., ltd.), methyl hydrogen polysiloxane (for example, KF-99P manufactured by Shin-Etsu Chemical Co., Ltd., SH1107C manufactured by Dow corning Toray), (dimethicone/methicone) copolymer (for example, KF-9901 manufactured by Shin-Etsu Chemical Co., Ltd.), methyl phenyl silicone (for example, KF-50-100cs manufactured by Shin-Etsu Chemical Co., Ltd.), amino modified silicone (for example, KF-8015 manufactured by Shin-Etsu Chemical Co., Ltd., JP-8500 Conditioning agent manufactured by Dow corning Toray, ADM6060 manufactured by wacker asahikasei silicone co., ltd.), triethoxysilylethyl polydimethylsiloxyethyl dimethicone (for example, KF-9908 manufactured by Shin-Etsu Chemical Co., Ltd.), and triethoxysilylethyl polydimethylsiloxyethyl hexyl dimethicone (for example, KF-9909 manufactured by Shin-Etsu Chemical Co., Ltd.).

The silane coupling agent includes vinyltris(2-methoxyethoxy)silane, vinyl trichlorosilane, vinyltrimethoxysilane, vinyltriethoxysilane, 2-(3,4 epoxy cyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropyl methyldimethoxysilane, 3-methacryloxypropyl trimethoxysilane, 3-methacryloxypropyl methyldiethoxysilane, 3-methacryloxypropyl triethoxysilane, 3-acryloxypropyl trimethoxysilane, N-2(aminoethyl) 3-aminopropylmethyldimethoxysilane, N-2(aminoethyl) 3-aminopropyltrimethoxysilane, N-2(aminoethyl) 3-aminopropyltriethoxysilane, 3-aminopropyltrimethoxysilane, 3-aminotriethoxysilane, 3-triethoxysilyl-N-(1,3 dimethylbutylidene) propylamine, N-phenyl-3-aminopropyltrimethoxysilane, N-(vinylbenzyl)-2-aminoethyl-3-aminopropyltrimethoxysilane hydrochloride, 3-ureidopropyltriethoxysilane, 3-chloropropyltrimethoxysilane, 3-mercaptopropylmethyldimethoxysilane, 3-mercaptopropyltrimethoxysilane, bis(triethoxysilylpropyl)tetrasulfide, 3-isocyanatepropyltriethoxysilane, tetramethoxysilane, tetraethoxysilane, methyltrimethoxysilane, methyltriethoxysilane, methyltriethoxysilane, phenyltriethoxysilane, hexamethyldisilazane, hexyltrimethoxysilane, and decyltrimethoxysilane.

The titanium coupling agent includes tetraisopropyl titanate, tetra-n-butyltitanate, butyltitanate dimer, tetra(2-ethylhexyl)titanate, tetramethyl titanate, titanium acetylacetonate, titanium tetraacetylacetonate, titanium ethylacetoacetate, titanium octanedioleate, titanium lactate, titanium triethanolaminato, and polyhydroxy titanium stearate.

The surface treatment is preferably done so that the surface treating amount is 1 to 10 wt % relative to the treated powder as whole. It is preferred to adjust the treating amount within the above-mentioned range because the smoothness and the humidity resistance can be improved to raise the dispersibility in a resin.

(Purpose)

The zinc oxide particle of the present disclosure may be used for a cosmetic, an ink, a coating, and a plastic in combination or mixed with other components. The zinc oxide particle especially has the above-mentioned properties so that the cosmetic containing the same which shows an excellent stability and ultraviolet shielding effect can be preferably obtained.

(Use in Cosmetic Field)

The cosmetic is not particularly limited. Cosmetics for ultraviolet prevention such as a sunscreen agent; cosmetics for base make up such as a foundation; and cosmetics for point make up such as a lipstick can be obtained by mixing the composite powder with any cosmetic raw material, as necessary. When used in cosmetics, excellent performances can be achieved because the composite powders have the ultraviolet shielding performance.

The cosmetic can be in any form, for example, a form of an oil-based cosmetic, a water-based cosmetic, an O/W type cosmetic, or a W/O type cosmetic.

The cosmetic may contain any water-based component or an oil-based component which can be used in the cosmetic field. The water-based component and the oil-based component may contain any component, including, but not limited to, for example, an oil solution, a surfactant, a humectant, a higher alcohol, a sequestering agent, a natural or synthetic polymer, a water-soluble or oil-soluble polymer, an ultraviolet shielding agent, various extracts, a coloring agent such as an organic dye, a preservative, an antioxidant, a colorant, a thickener, a pH adjuster, a perfume, a cooling-sensation agent, an antiperspirant, a bactericidal agent, a skin activating agent, and various powders.

Examples of the oil solution include, but not limited to, for example, natural animal and plant fats (for example, olive oil, mink oil, castor oil, palm oil, beef tallow, evening primrose oil, coconut oil, castor oil, cacao oil, and macadamia nut oil); waxes (for example, jojoba oil, beeswax, lanolin, carnauba wax, and candelilla wax); higher alcohols (for example, lauryl alcohol, stearyl alcohol, cetyl alcohol, and oleyl alcohol); higher fatty acids (for example, lauric acid, palmitic acid, stearic acid, oleic acid, behenic acid, and lanolin fatty acid); higher aliphatic hydrocarbons (for example, liquid paraffin, solid paraffin, squalane, vaseline, ceresin, and microcrystalline wax); synthetic ester oils (for example, butyl stearate, hexyl laurate, diisopropyl adipate, diisopropyl sebacate, octyldodecyl myristate, isopropyl myristate, isopropyl palmitate, isopropyl myristate, cetyl isooctanoate, and neopentyl glycol dicaprate); and silicone derivatives (for example, silicone oils such as methyl silicone and methyl phenyl silicone). Further, an oil-soluble vitamin, a preservative, or a whitening agent may be blended.

Examples of the surfactant include a lipophilic nonionic surfactant and a hydrophilic nonionic surfactant. Examples of the lipophilic nonionic surfactant include, but not limited to, for example, sorbitan monooleate, sorbitan monoisostearate, sorbitan monolaurate, sorbitan monopalmitate, sorbitan monostearate, sorbitan sesquioleate, sorbitan trioleate, sorbitan fatty acid esters such as diglycerol sorbitan penta-2-ethylhexylate and diglycerol sorbitan tetra-2-ethylhexylate, glycerin fatty acids such as glycerol mono-cottonseed oil fatty acid, glycerol monoerucate, glycerol sesquioleate, glycerol monostearate, $\alpha,\alpha'$-glycerol oleate pyroglutamate, and glycerol monostearate malate; propylene glycol fatty acid esters such as propylene glycol monostearate; hydrogenated castor oil derivatives; and glycerol alkyl ethers.

Examples of the hydrophilic nonionic surfactant include, but not limited to, for example, POE sorbitan fatty acid esters such as POE sorbitan monooleate, POE sorbitan monostearate, and POE sorbitan tetraoleate; POE sorbit fatty acid esters such as POE sorbit monolaurate, POE sorbit monooleate, POE sorbit pentaoleate, and POE sorbit monostearate; POE glycerin fatty acid esters such as POE glycerin monostearate, POE glycerin monoisostearate, and POE glycerin triisostearate; POE fatty acid esters such as POE monooleate, POE distearate, POE monodioleate, and distearic acid ethylene glycol; POE alkyl ethers such as POE lauryl ether, POE oleyl ether, POE stearyl ether, POE behenyl ether, POE 2-octyl dodecyl ether, and POE cholestanol ether; POE alkyl phenyl ethers such as POE octyl phenyl ether, POE nonyl phenyl ether, and POE dinonyl phenyl ether; Pluaronic types such as Pluronic; POE/POP alkyl ethers such as POE/POP cetyl ether, POE/POP2-decyl tetradecyl ether, POE/POP monobutyl ether, POE/POP hydrogenated lanolin, and POE/POP glycerin ether; tetra POE/tetra POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleic acid; POE beeswax/lanolin derivatives such as POE sorbit beeswax; alkanolamides such as coconut oil fatty acid diethanolamide, lauric acid monoethanolamide, and fatty acid isopropanolamide; POE propylene glycol fatty acid esters, POE alkylamines, POE fatty acid amides, sucrose fatty acid esters, POE nonyl phenyl formaldehyde condensation products, alkyl ethoxydimethylamine oxides, and trioleyl phosphates.

Any other surfactant may be blended, including, for example, anionic surfactants such as fatty acid soaps, higher alkyl sulfate ester salts, POE lauryl sulfate triethanolamine, and alkyl ether sulfate ester salts; cationic surfactants such as alkyl trimethyl ammonium salts, alkyl pyridinium salts, alkyl quaternized ammonium salts, alkyl dimethyl benzylammonium salts, POE alkylamines, alkylamine salts, and polyamine fatty acid derivatives; and amphoteric surfactants such as an imidazoline-based amphoteric surfactant and a betaine-based surfactant, as long as the surfactant does not affect the stability and skin irritation.

Examples of the humectant include, but not limited to, for example, xylitol, sorbitol, maltitol, chondroitin sulfate, hyaluronic acid, mucoitinsulfuric acid, caronic acid, atelocollagen, cholesteryl-12-hydroxystearate, sodium lactate, bile salt, dl-pyrrolidone carboxylate salts, short chain soluble collagen, (EO)PO adducts of diglycerin, *Rosa Roxburghii* Fruit extract, yarrow extract, and melilot extract.

Examples of the higher alcohol include, but not limited to, for example, linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyl tetradecinol, lanolin alcohol, cholesterol, phytosterol, hexyldodecanol, isostearyl alcohol, and octyl dodecanol.

Examples of the sequestering agent include, but not limited to, for example, 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

Examples of the natural water-soluble polymer include, but not limited to, for example, plant polymers such as gum arabic, tragacanth gum, galactan, guar gum, carob gum, karaya gum, carrageenan, pectin, agar, quince seed (*Cydonia oblonga*), algae colloid (brown alga extract), starch (rice, corn, potato, wheat), and glycyrrhizinic acid; microbial polymers such as xanthan gum, dextran, succinoglycan, and pullulan; and animal polymers such as collagen, casein, albumin, and gelatin.

Examples of the semisynthetic water-soluble polymer include, but not limited to, for example, starch polymers such as carboxymethyl starch and methyl hydroxypropyl starch; cellulose polymers such as methylcellulose, nitrocellulose, ethylcellulose, methyl hydroxypropyl cellulose, hydroxyethyl cellulose, cellulose sodium sulfate, hydroxypropyl cellulose, sodium carboxymethyl cellulose (CMC), crystalline cellulose, and cellulose powder; and alginate polymers such as sodium alginate and alginic acid propylene glycol ester.

Examples of the synthetic water-soluble polymer include, but not limited to, for example, vinyl polymers such as polyvinyl alcohol, polyvinyl methyl ether, and polyvinylpyrrolidone; polyoxyethylene polymers such as polyethylene glycol 20,000, 40,000, and 60,000; copolymers such as a polyoxyethylene polyoxypropylene copolymer; acrylic polymers such as sodium polyacrylate, polyethyl acrylate, and polyacrylamide; polyglycerin, polyethylenimine, cationic polymer, carboxyvinyl polymer, alkyl-modified carboxyvinyl polymer, (hydroxyethyl acrylate/acryloyl dimethyl taurine Na) copolymer, (acrylate Na/acryloyl dimethyl taurine Na) copolymer, (acryloyl dimethyl taurine ammonium/vinylpyrrolidone) copolymer, (acryloyl dimethyl taurine ammonium methacrylate beheneth-25) crosspolymer.

Examples of the inorganic water-soluble polymer include, but not limited to, for example, bentonite, magnesium aluminum silicate (Veegum), laponite, hectorite, and silicic anhydride.

Examples of the ultraviolet shielding agent include, but not limited to, for example, benzoic acid-based ultraviolet shielding agents such as p-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid-based ultraviolet shielding agents such as homomenthyl-N-acetyl anthranilate; salicylic acid-based ultraviolet shielding agents such as amyl salicylate, menthyl salicylate, homomenthyl salicylate, octyl salicylate, phenyl salicylate, benzyl salicylate, and p-isopropanol phenyl salicylate; cinnamic acid-based ultraviolet shielding agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-diparamethoxy cinnamate; benzophenone-based ultraviolet shielding agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methyl benzophenone, 2-hydroxy-4-methoxybenzophenone-5-sulfonate, 4-phenyl benzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methyl benzoxazole, 2,2'-hydroxy-5-methyl phenyl benzotriazole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane, and 5-(3,3-dimethyl-2-norbornylidene)-3-pentan-2-one.

Examples of the other chemical component include, but not limited to, for example, vitamins such as vitamin A oil, retinol, retinol palmitate, inosit, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), dl-α-tocopherol, DL-α-tocopherol acetate, pantothenic acid, and biotin; hormones such as estradiol and ethinyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor; sulfur, lysozyme chloride, and pyridoxine chloride.

Examples of various extracts include, but not limited to, for example, *Houttuynia cordata* extract, Phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

Examples of various powders include luster color pigments such as red iron oxide, yellow iron oxide, black iron oxide, mica titanium, iron oxide-coated mica titanium, and titanium oxide-coated glass flake; inorganic powders such as mica, talc, kaolin, sericite, titanium dioxide, and silica; and organic powders such as polyethylene powder, nylon powder, crosslinked polystyrene, cellulose powder, and silicone powder. Preferably, some or all of powder components are hydrophobized with a material such as a silicone, a fluorine compound, a metallic soap, an oil solution, or an acyl glutamic acid salt by a known method in order to improve sensory characteristics and makeup retainability. Further, a composite powder other than the composite powder of the present disclosure may be blended and used.

(Use in Ink Field)

When the zinc oxide powder of the present disclosure is used as a component added to inks, colored pigments such as titanium oxide, red iron oxide, antimony red, cadmium yellow, cobalt blue, prussian blue, ultramarine, carbon black, and graphite; and extender pigments such as calcium carbonate, kaolin, clay, barium sulfate, aluminum hydroxide, and talc may be used in combination. Further, the above zinc oxide powder can be used with the organic pigment including pigment components such as a soluble azo pigment, an insoluble azo pigment, an azo lake pigment, a condensed azo pigment, a copper phthalocyanine pigment, and a condensed polycyclic pigment; binder resins such as a shellac resin, an acrylic resin, a styrene-acrylic resin, a styrene-maleic acid resin, a styrene-acrylic-maleic acid resin, a polyurethane resin, a polyester resin, and a polyamide resin; and water-miscible organic solvents.

(Use in Coating Field)

When the zinc oxide powder of the present disclosure is used as a component added to coating compositions, it can be used with film-forming resins such as an acrylic resin, a polyester resin, and an epoxy resin; various pigments such as a colored pigment, a extender pigment, and a luster pigment; a curing catalyst, a surface control agent, an antifoaming agent, a pigment dispersant, a plasticizer, a film-forming aid, an ultraviolet absorption agent, an antioxidant, and the like. A resin in the coating may be a curable or uncurable resin.

EXAMPLES

Hereinafter, the present disclosure will be explained with reference to examples. However, the present disclosure is not limited to these examples.

Example 1

Figure 2:
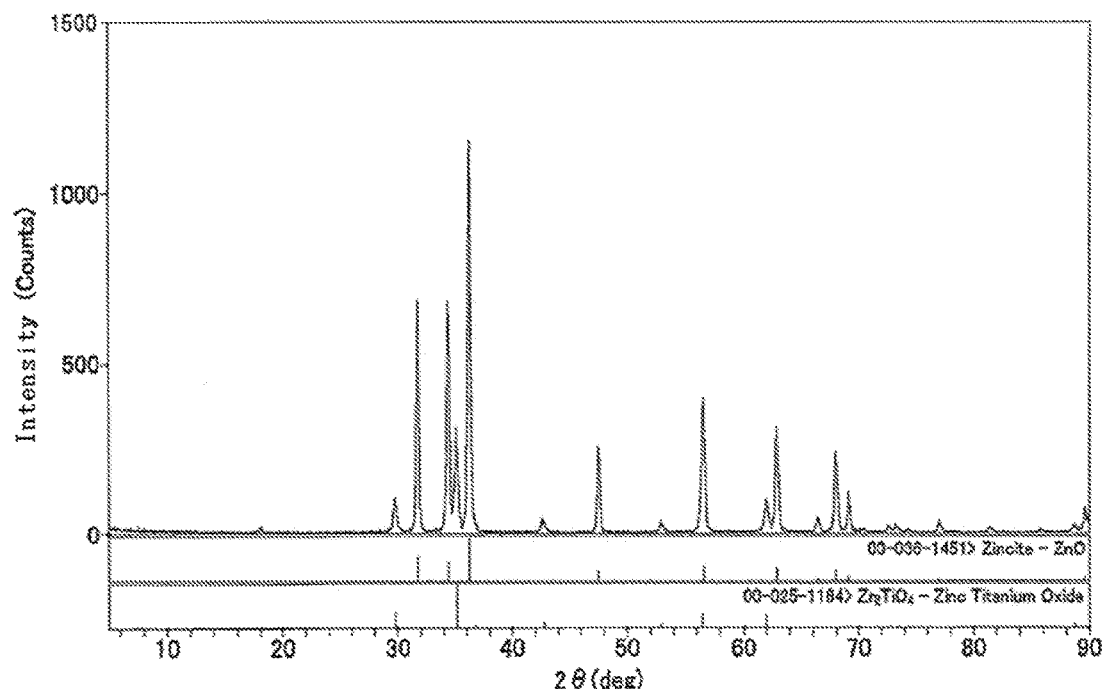
FIG. 2 is an X-ray diffraction spectrum of $Zn_2TiO_4$-coated zinc oxide particles obtained in example 1.

Hexagonal plate-shaped zinc oxide having a primary particle diameter of 1.05 μm (XZ-1000F, manufactured by Sakai Chemical Industry Co., Ltd.) 150 g was added to water 723.21 g and stirred sufficiently to prepare a water-based slurry with ZnO concentration of 200 g/l. Then, after the slurry was stirred and heated to 40° C., the pH of the slurry was adjusted to 10 by adding 5 wt % of NaOH aqueous solution while maintaining the temperature. Next, 330 ml of titanium sulfate aqueous solution with $TiO_2$ concentration of 45.5 g/l (an amount corresponding to 10 wt parts relative to the matrix ZnO in terms of $TiO_2$) and 5 wt % of NaOH aqueous solution for neutralizing the titanium sulfate aqueous solution were added simultaneously to the slurry over 180 minutes while the temperature was maintained at 40° C. and the pH was maintained at 10. After the completion of the neutralizing, the mixture was aged for 30 minutes, filtered, and water washed. Then, the mixture was dried at 120° C. for 12 hours to obtain titanium hydroxide-coated zinc oxide particle, which is composed of the matrix hexagonal plate-shaped zinc oxide particle having a primary particle diameter of 1.05 μm and a covering layer of titanium hydroxide on the surface thereof. Then, the obtained titanium hydroxide-coated zinc oxide particles were baked at 700° C. for 2 hours in an electric furnace to obtain $Zn_2TiO_4$-coated hexagonal plate-shaped zinc oxide particles having a primary particle diameter of 1.07 μm. The size and form of the obtained particles were observed with a transmission electron microscope JEM-2100 (manufactured by JEOL Ltd.). The obtained electron microscope photograph is shown in FIG. 1. The obtained particles were analyzed by using an X-ray diffractometer Ultima III (manufactured by Rigaku Corporation). The X-ray diffraction spectra is shown in FIG. 2, and the physical properties of the particle and the coating film are shown in Table 1. The ratio of (ultraviolet shielding ratio 1 of a coating film containing the coated zinc oxide particle (%)/(ultraviolet shielding ratio 1 of a coating film containing the raw zinc oxide particle which is the matrix of the coated zinc oxide particle (%)) is 1.6 and the ratio of (ultraviolet shielding ratio 2 of a coating film containing the coated zinc oxide particle (%)/(ultraviolet shielding ratio 2 of a coating film containing the raw zinc oxide particle which is the matrix of the coated zinc oxide particle (%)) is 1.2, and it was confirmed that the obtained zinc oxide particle has more improved ultraviolet shielding property for UV-B radiation and UV-A radiation than the matrix raw zinc oxide particle.

Example 2

Figure 3:
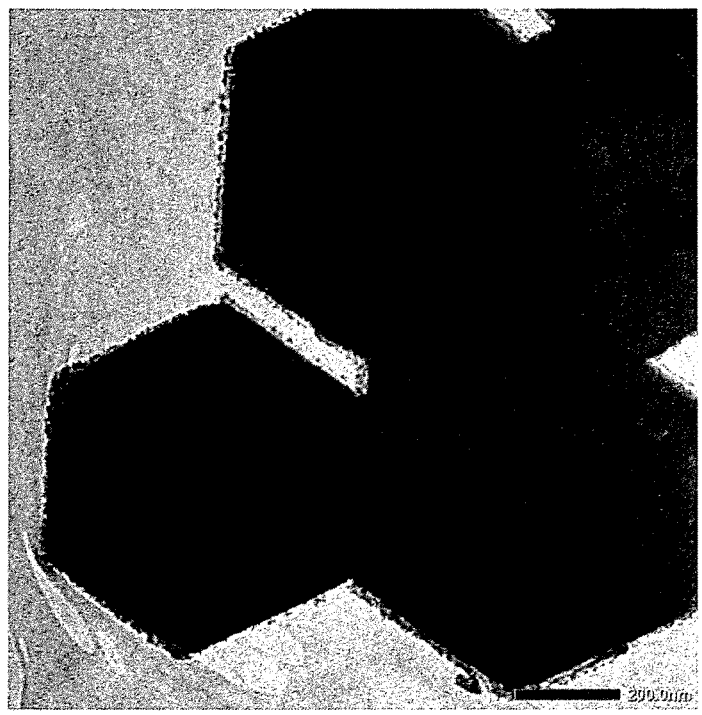
FIG. 3 is a transmission electron microscope photograph of $ZnFe_2O_4$-coated zinc oxide particles obtained in example 2.
Figure 4:
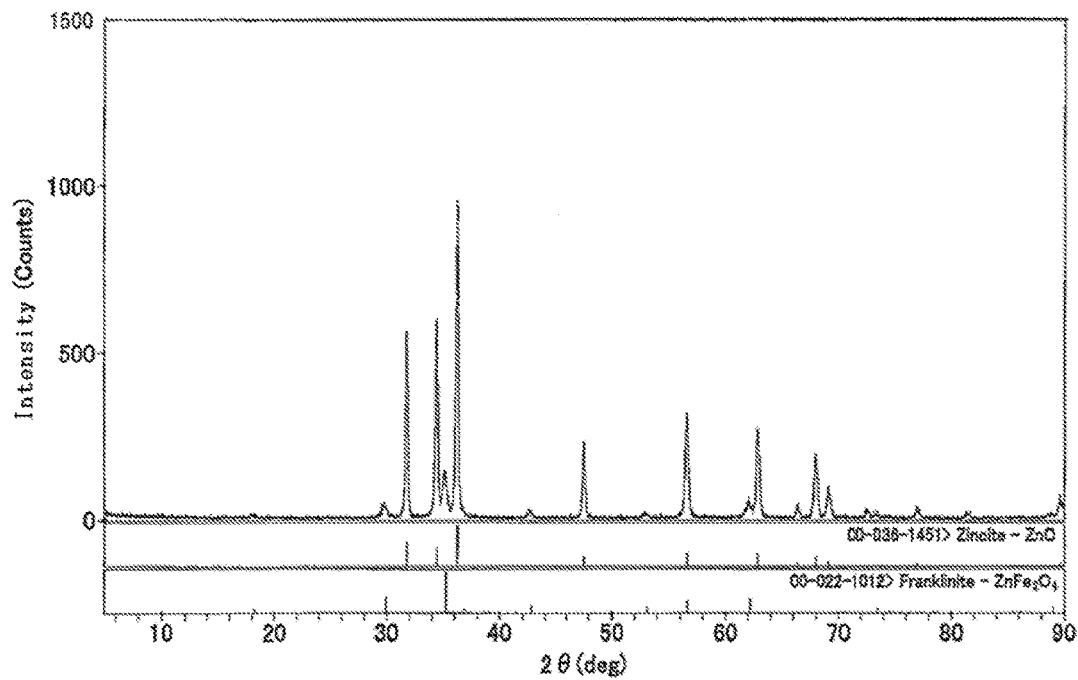
FIG. 4 is an X-ray diffraction spectrum of $ZnFe_2O_4$-coated zinc oxide particles obtained in example 2.

Hexagonal plate-shaped zinc oxide having a primary particle diameter of 1.05 μm (XZ-1000F, manufactured by Sakai Chemical Industry Co., Ltd.) 150 g was added to water 723.21 g and stirred sufficiently to prepare a water-based slurry with ZnO concentration of 200 g/l. Then, after the slurry was stirred and heated to 30° C., the pH of the slurry was adjusted to 10 by adding 5 wt % of NaOH aqueous solution while maintaining the temperature. Next, 387 ml of iron sulfate (iron (I) sulfate heptahydrate) aqueous solution with $Fe_2O_3$ concentration of 38.8 g/l (an amount corresponding to 10 wt parts relative to the matrix ZnO in terms of $Fe_2O_3$) and 5 wt % of NaOH aqueous solution for neutralizing the iron sulfate aqueous solution were added simultaneously to the slurry over 180 minutes while the temperature was maintained at 30° C. and the pH was maintained at 10. After the completion of the neutralizing, the mixture was aged for 30 minutes, filtered, and water washed. Then, the mixture was dried at 120° C. for 12 hours to obtain iron hydroxide-coated zinc oxide particle, which is composed of the matrix hexagonal plate-shaped zinc oxide particle having a primary particle diameter of 1.05 μm and a covering layer of iron hydroxide on the surface thereof. Then, the obtained iron hydroxide-coated zinc oxide particles were baked at 600° C. for 2 hours in an electric furnace to obtain $ZnFe_2O_4$-coated hexagonal plate-shaped zinc oxide particles having a primary particle diameter of 1.06 μm. The size and form of the obtained particles were observed with a transmission electron microscope JEM-2100 (manufactured by JEOL Ltd.). The obtained electron microscope photograph is shown in FIG. 3. The obtained particles were analyzed by using an X-ray diffractometer Ultima III (manufactured by Rigaku Corporation). The X-ray diffraction spectra is shown in FIG. 4, and the physical properties of the particle and the coating film are shown in Table 1. The ratio of (ultraviolet shielding ratio 1 of a coating film containing the coated zinc oxide particle (%)/(ultraviolet shielding ratio 1 of a coating film containing the raw zinc oxide particle which is the matrix of the coated zinc oxide particle (%)) is 1.7 and the ratio of (ultraviolet shielding ratio 2 of a coating film containing the coated zinc oxide particle (%)/(ultraviolet shielding ratio 2 of a coating film containing the raw zinc oxide particle which is the matrix of the coated zinc oxide particle (%)) is 1.3, and it was confirmed that the obtained zinc oxide particle has more improved ultraviolet shielding property for UV-B radiation and UV-A radiation than the matrix raw zinc oxide particle.

Example 3

Figure 5:
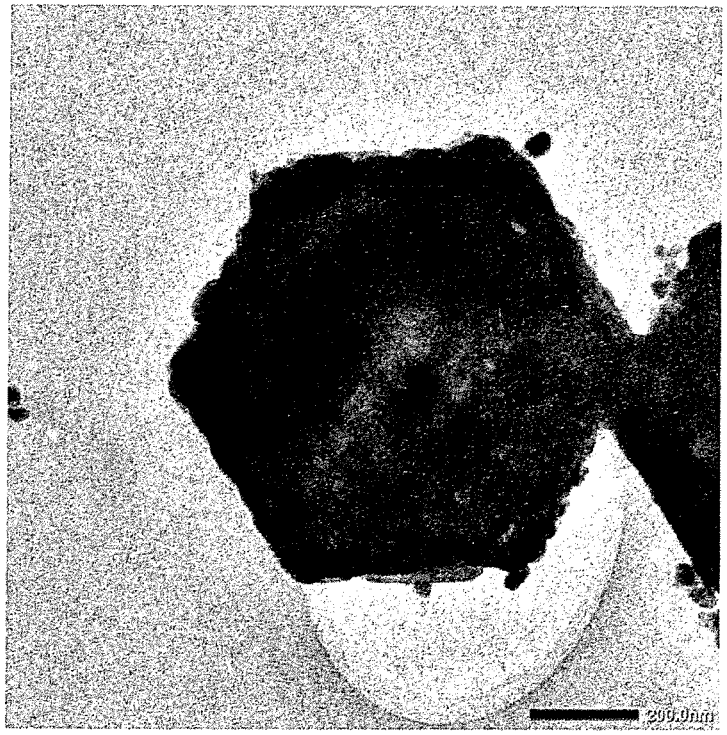
FIG. 5 is a transmission electron microscope photograph of $Zn_2TiO_4+ZnFe_2O_4$-coated zinc oxide particles obtained in example 3.
Figure 6:
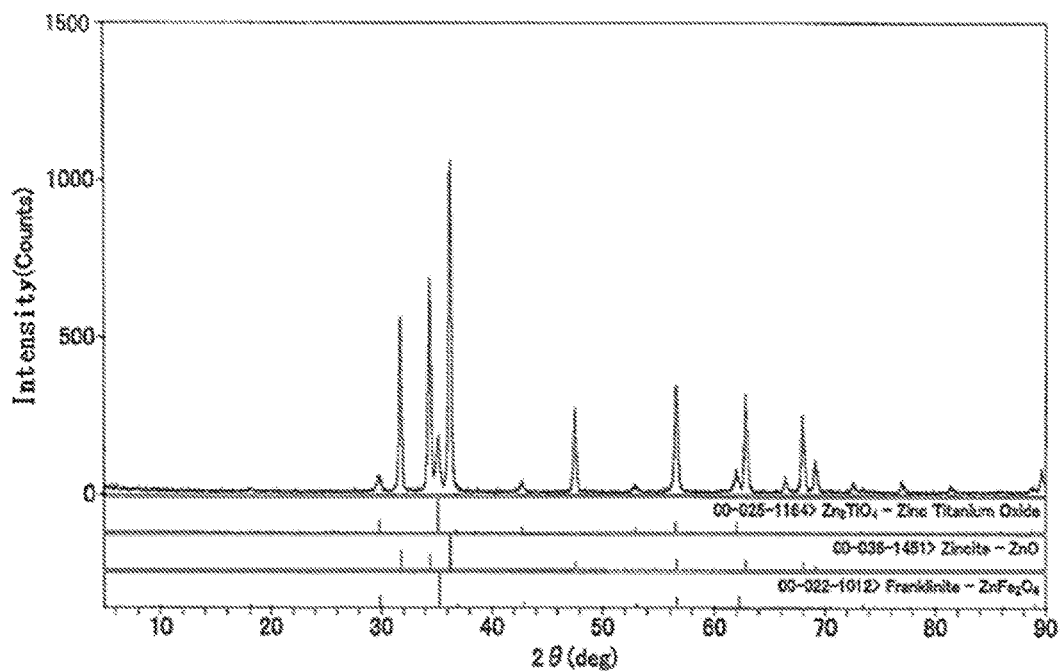
FIG. 6 is an X-ray diffraction spectrum of $Zn_2TiO_4+ZnFe_2O_4$-coated zinc oxide particles obtained in example 3.

Hexagonal plate-shaped zinc oxide having a primary particle diameter of 1.05 μm (XZ-1000F, manufactured by Sakai Chemical Industry Co., Ltd.) 150 g was added to water 723.21 g and stirred sufficiently to prepare a water-based slurry with ZnO concentration of 200 g/l. Then, after the slurry was stirred and heated to 40° C., the pH of the slurry was adjusted to 10 by adding 5 wt % of NaOH aqueous solution while maintaining the temperature. Next, 165 ml of titanium sulfate aqueous solution with $TiO_2$ concentration of 45.5 g/l (an amount corresponding to 5 wt parts relative to the matrix ZnO in terms of $TiO_2$), 194 ml of iron sulfate (iron (I) sulfate heptahydrate) aqueous solution with $Fe_2O_3$ concentration of 38.8 g/l (an amount corresponding to 5 wt parts relative to the matrix ZnO in terms of $Fe_2O_3$), and 5 wt % of NaOH aqueous solution for neutralizing the titanium sulfate aqueous solution and the iron sulfate aqueous solution were added simultaneously to the slurry over 180 minutes while the temperature was maintained at 40° C. and the pH was maintained at 10. After the completion of the neutralizing, the mixture was aged for 30 minutes, filtered, and water washed. Then, the mixture was dried at 120° C. for 12 hours to obtain titanium hydroxide and iron hydroxide-coated zinc oxide particle, which is composed of the matrix hexagonal plate-shaped zinc oxide particle having a primary particle diameter of 1.05 μm and a covering layer of titanium hydroxide and iron hydroxide on the surface thereof. Then, the obtained titanium hydroxide and iron hydroxide-coated zinc oxide particles were baked at 700° C. for 2 hours in an electric furnace to obtain $Zn_2TiO_4$+$ZnFe_2O_4$-coated hexagonal plate-shaped zinc oxide particles having a primary particle diameter of 1.07 μm. The size and form of the obtained particles were observed with a transmission electron microscope JEM-2100 (manufactured by JEOL Ltd.). The obtained electron microscope photograph is shown in FIG. 5. The obtained particles were analyzed by using an X-ray diffractometer Ultima III (manufactured by Rigaku Corporation). The X-ray diffraction spectra is shown in FIG. 6, and the physical properties of the particle and the coating film are shown in Table 1. The ratio of (ultraviolet shielding ratio 1 of a coating film containing the coated zinc oxide particle (%)/(ultraviolet shielding ratio 1 of a coating film containing the raw zinc oxide particle which is the matrix of the coated zinc oxide particle (%)) is 1.6 and the ratio of (ultraviolet shielding ratio 2 of a coating film containing the coated zinc oxide particle (%)/(ultraviolet shielding ratio 2 of a coating film containing the raw zinc oxide particle which is the matrix of the coated zinc oxide particle (%)) is 1.2, and it was confirmed that the obtained zinc oxide particle has more improved ultraviolet shielding property for UV-B radiation and UV-A radiation than the matrix raw zinc oxide particle.

Example 4

Figure 7:
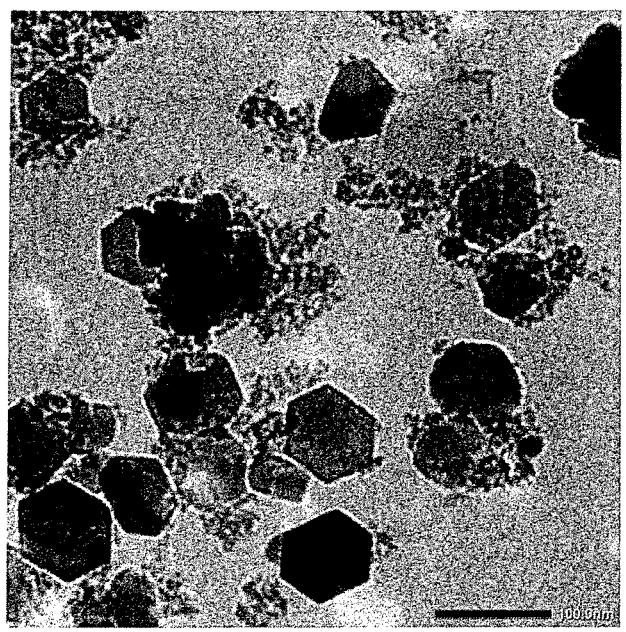
FIG. 7 is a transmission electron microscope photograph of $ZnFe_2O_4$-containing zinc oxide particles obtained in example 4.
Figure 8:
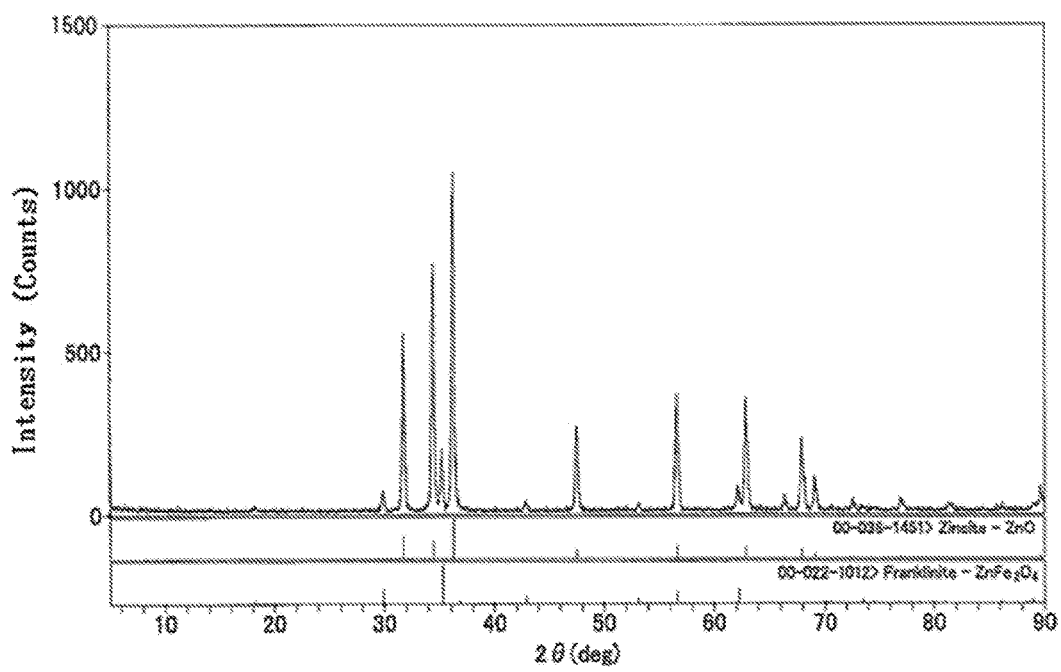
FIG. 8 is an X-ray diffraction spectrum of $ZnFe_2O_4$-containing zinc oxide particles obtained in example 4.

Zinc acetate dihydrate (zinc acetate, manufactured by Hosoi Chemical Industry Co., Ltd.) 66.51 g was dissolved in water to prepare a zinc acetate aqueous solution 1200 ml with zinc acetate dihydrate concentration of 0.5 mol/l. Next, iron (II) acetate (manufactured by Wako Pure Chemical Industries, Ltd.) 9.68 g was added to the zinc acetate aqueous solution 1200 ml and dissolved perfectly. Then, zinc oxide having a primary particle diameter of 0.02 μm (FINEX-50 manufactured by Sakai Chemical Industry Co., Ltd.,) 40 g was repulped to the aqueous solution, thereby forming a slurry. The slurry was stirred and heated to 95° C. over 65 minutes, and aged for 1 hour at 95° C. with stirring. After aging, the slurry was filtered and washed with water. Subsequently, the obtained solid was repulped in 3 liters of water to form a slurry, and the slurry was heated to 95° C. with stirring, and heated and washed at 95° C. for 30 minutes with stirring. After heating and washing, the slurry was filtered, washed with water, and dried at 110° C. for 12 hours to obtain iron hydroxide-containing hexagonal plate-shaped zinc oxide particles. Then, the obtained iron hydroxide-containing zinc oxide particles were baked at 600° C. for 2 hours in an electric furnace to obtain $ZnFe_2O_4$-containing zinc oxide particles having a primary particle diameter of 0.07 μm. The size and form of the obtained particles were observed with a transmission electron microscope JEM-2100 (manufactured by JEOL Ltd.). The obtained electron microscope photograph is shown in FIG. 7. The obtained particles were analyzed by using an X-ray diffractometer Ultima III (manufactured by Rigaku Corporation). The X-ray diffraction spectra is shown in FIG. 8, and the physical properties of the particle and the coating film are shown in Table 1.

Comparative Example 1

Figure 9:
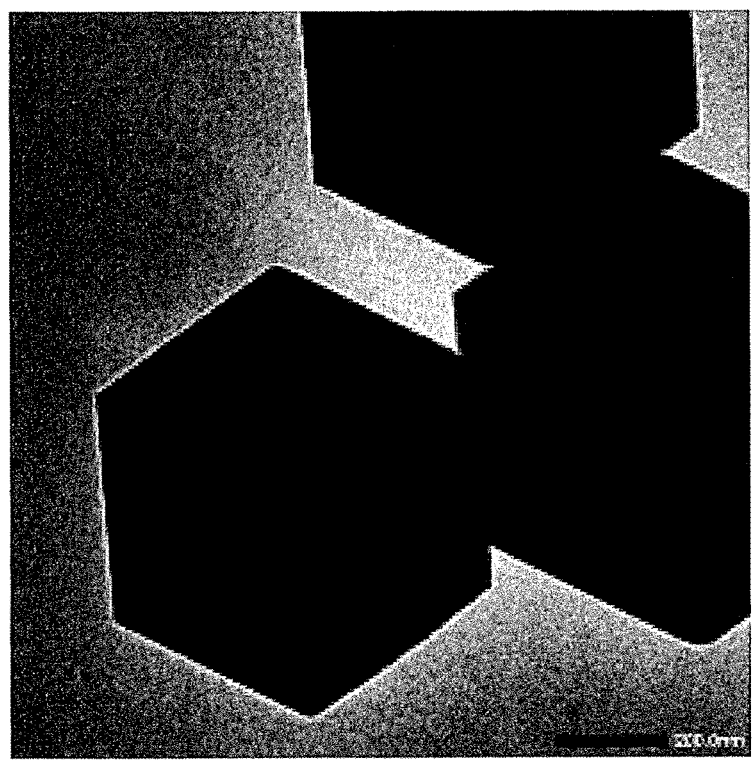
FIG. 9 is a transmission electron microscope photograph of matrix hexagonal plate-shaped zinc oxide particles in comparative example 1.

Hexagonal plate-shaped zinc oxide having a primary particle diameter of 1.05 μm (XZ-1000F, manufactured by Sakai Chemical Industry Co.) was used as ultraviolet shielding agent for comparison. The transmission electron microscope photograph of the particles was shown in FIG. 9. The physical properties of the particle and the coating film are shown in Table 1. Further, this particle is the raw zinc oxide particle to be used as the matrix of the coated zinc oxide particles obtained in examples 1, 2, and 3.

Comparative Example 2

Figure 10:
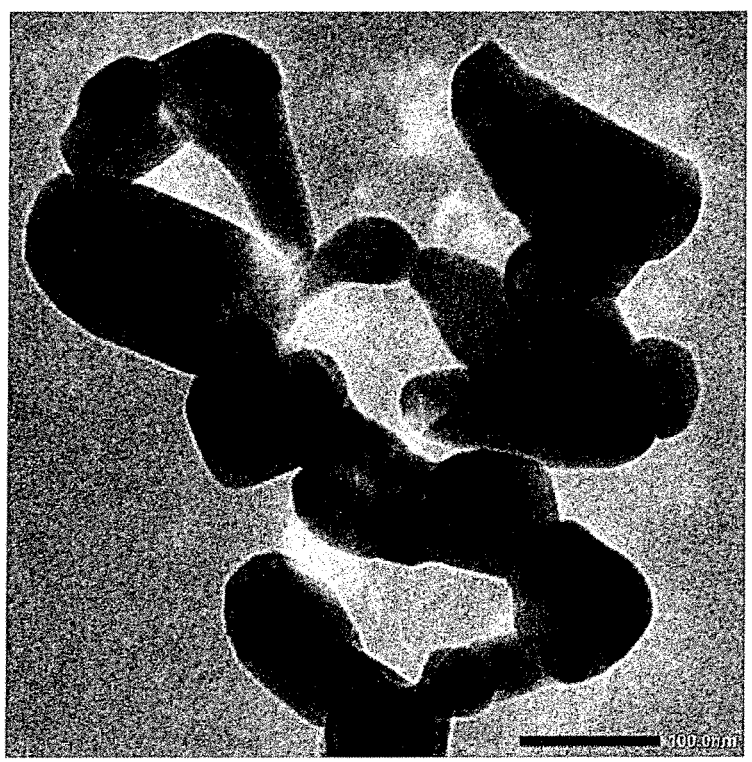
FIG. 10 is a transmission electron microscope photograph of matrix indefinite-shaped zinc oxide particles in comparative example 2.

Zinc oxide having a primary particle diameter of 0.02 μm (FINEX-50, manufactured by Sakai Chemical Industry Co.) 50 g was baked at 550° C. for 2 hours in an electric furnace to obtain indefinite-shaped zinc oxide particles having a primary particle diameter of 0.11 μm. Then, the obtained particles were used as ultraviolet shielding agent for comparison. The obtained transmission electron microscope photograph of the particles was shown in FIG. 10. The physical properties of the particle and the coating film are shown in Table 1. Further, this particle is the raw zinc oxide particle to be used as the matrix of the coated zinc oxide particles obtained in comparative examples 3 and 4.

Comparative Example 3

Figure 11:
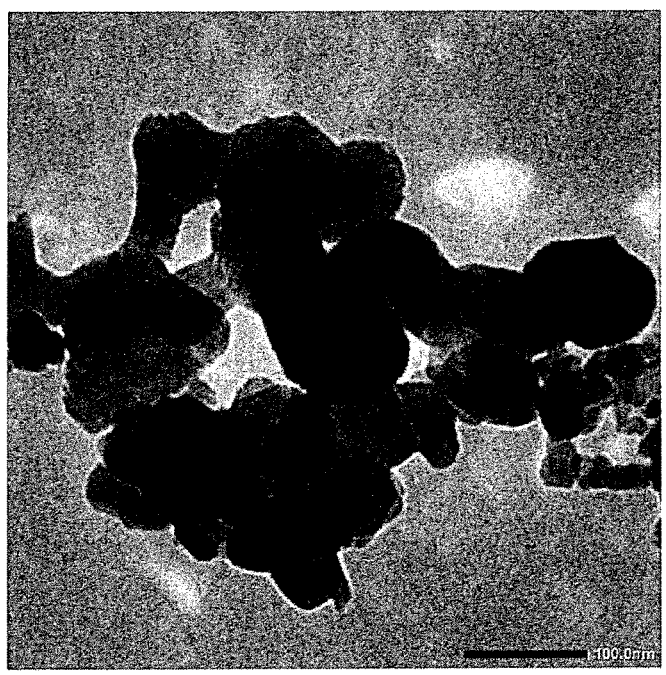
FIG. 11 is a transmission electron microscope photograph of $Zn_2TiO_4$-coated zinc oxide particles obtained in comparative example 3.
Figure 12:
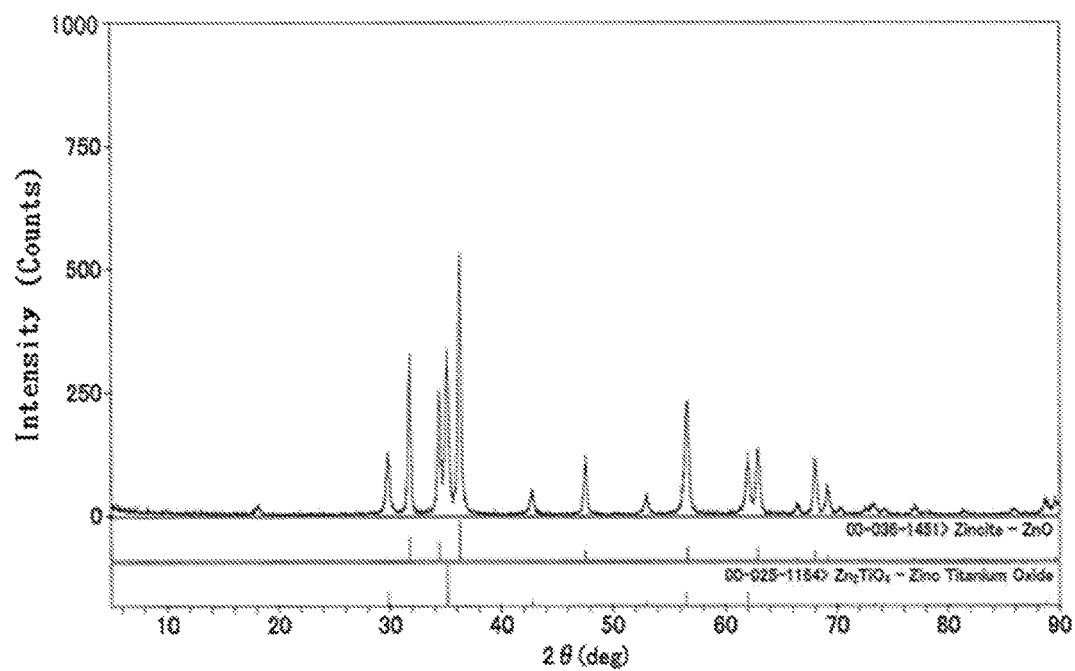
FIG. 12 is an X-ray diffraction spectrum of $Zn_2TiO_4$-coated zinc oxide particles obtained in comparative example 3.

Indefinite-shaped zinc oxide particle 30 g having a particle diameter of 0.11 μm obtained in comparative example 2 was added to water 144.64 g and stirred sufficiently to prepare a water-based slurry with ZnO concentration of 200 g/l. Then, after the slurry was stirred and heated to 40° C., the pH of the slurry was adjusted to 10 by adding 5 wt % of NaOH aqueous solution while maintaining the temperature. Next, 132 ml of titanium sulfate aqueous solution with $TiO_2$ concentration of 45.5 g/l (an amount corresponding to 20 wt parts relative to the matrix ZnO in terms of $TiO_2$) and 5 wt % of NaOH aqueous solution for neutralizing the titanium sulfate aqueous solution were added simultaneously to the slurry over 180 minutes while the temperature was maintained at 40° C. and the pH was maintained at 10. After the completion of the neutralizing, the mixture was aged for 30 minutes, filtered, and water washed. Then, the mixture was dried at 120° C. for 12 hours to obtain titanium hydroxide-coated zinc oxide particles composed of the matrix indefinite-shaped zinc oxide particle having a primary particle diameter of 0.11 μm and a covering layer of titanium hydroxide on the surface thereof. Next, the obtained titanium hydroxide-coated zinc oxide particles were baked at 700° C. for 2 hours in an electric furnace to obtain $Zn_2TiO_4$-coated zinc oxide particles having a primary particle diameter of 0.12 μm. The size and form of the obtained particles were observed with a transmission electron microscope JEM-2100 (manufactured by JEOL Ltd.). The obtained electron microscope photograph is shown in FIG. 11. The obtained particles were analyzed by using an X-ray diffractometer Ultima III (manufactured by Rigaku Corporation). The X-ray diffraction spectra is shown in FIG. 12, and the physical properties of the particle and the coating film are shown in Table 1. The ratio of (ultraviolet shielding ratio 1 of a coating film containing the coated zinc oxide particle (%))/(ultraviolet shielding ratio 1 of a coating film containing the raw zinc oxide particle which is the matrix of the coated zinc oxide particle (%)) is 1.0 and the ratio of (ultraviolet shielding ratio 2 of a coating film containing the coated zinc oxide particle (%))/(ultraviolet shielding ratio 2 of a coating film containing the raw zinc oxide particle which is the matrix of the coated zinc oxide particle (%)) is 0.9, and it was confirmed that the obtained zinc oxide particle has not more improved ultraviolet shielding property for UV-B radiation and UV-A radiation than the matrix raw zinc oxide particle.

Comparative Example 4

Figure 13:
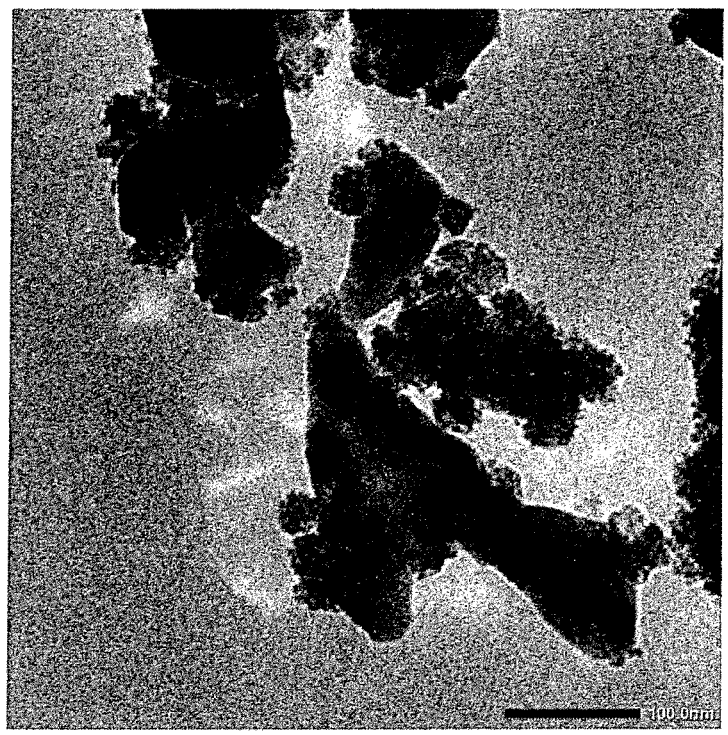
FIG. 13 is a transmission electron microscope photograph of $ZnFe_2O_4$-coated zinc oxide particles obtained in comparative example 4.
Figure 14:
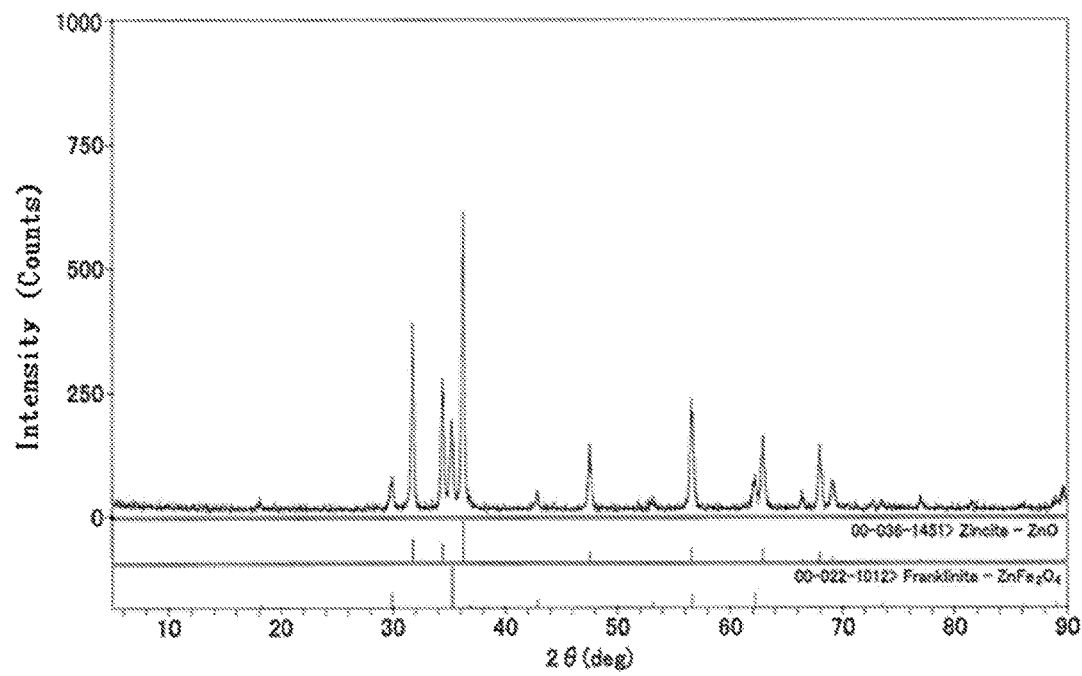
FIG. 14 is an X-ray diffraction spectrum of $ZnFe_2O_4$-coated zinc oxide particles obtained in comparative example 4.

Indefinite-shaped zinc oxide particle 30 g having a particle diameter of 0.11 μm obtained in comparative example 2 was added to water 144.64 g and stirred sufficiently to prepare a water-based slurry with ZnO concentration of 200 g/l. Then, after the slurry was stirred and heated to 30° C., the pH of the slurry was adjusted to 10 by adding 5 wt % of NaOH aqueous solution while maintaining the temperature. Next, 154 ml of iron sulfate (iron (I) sulfate heptahydrate) aqueous solution with $Fe_2O_3$ concentration of 38.8 g/l (an amount corresponding to 20 wt parts relative to the matrix ZnO in terms of $Fe_2O_3$) and 5 wt % of NaOH aqueous solution for neutralizing the iron sulfate aqueous solution were added simultaneously to the slurry over 180 minutes while the temperature was maintained at 30° C. and the pH was maintained at 10. After the completion of the neutralizing, the mixture was aged for 30 minutes, filtered, and water washed. Then, the mixture was dried at 120° C. for 12 hours to obtain iron hydroxide-coated zinc oxide particles composed of the matrix indefinite-shaped zinc oxide particle having a primary particle diameter of 0.11 μm and a covering layer of iron hydroxide on the surface thereof. Next, the obtained iron hydroxide-coated zinc oxide particles were baked at 600° C. for 2 hours in an electric furnace to obtain $ZnFe_2O_4$-coated zinc oxide particles having a primary particle diameter of 0.11 μm. The size and form of the obtained particles were observed with a transmission electron microscope JEM-2100 (manufactured by JEOL Ltd.). The obtained electron microscope photograph is shown in FIG. 13. The obtained particles were analyzed by using an X-ray diffractometer Ultima III (manufactured by Rigaku Corporation). The X-ray diffraction spectra is shown in FIG. 14, and the physical properties of the particle and the coating film are shown in Table 1. The ratio of (ultraviolet shielding ratio 1 of a coating film containing the coated zinc oxide particle (%))/(ultraviolet shielding ratio 1 of a coating film containing the raw zinc oxide particle which is the matrix of the coated zinc oxide particle (%)) is 1.0 and the ratio of (ultraviolet shielding ratio 2 of a coating film containing the coated zinc oxide particle (%))/(ultraviolet shielding ratio 2 of a coating film containing the raw zinc oxide particle which is the matrix of the coated zinc oxide particle (%)) is 1.0, and it was confirmed that the obtained zinc oxide particle has not more improved ultraviolet shielding property for UV-B radiation and UV-A radiation than the matrix raw zinc oxide particle.

TABLE 1

| | | | Ex. 1 | Ex. 2 | Ex. 3 | Ex. 4 | Compar. Ex. 1 | Compar. Ex. 2 | Compar. Ex. 3 | Compar. Ex. 4 |
|---|---|---|---|---|---|---|---|---|---|---|
| Physical property of particle | Composition of obtained particle | | ZnO + $Zn_2TiO_4$ | ZnO + $ZnFe_2O_4$ | ZnO + $Zn_2TiO_4$ + $ZnFe_2O_4$ | ZnO + $ZnFe_2O_4$ | ZnO | ZnO | ZnO + $Zn_2TiO_4$ | ZnO + $ZnFe_2O_4$ |
| | Particle shape | | Hexagonal | Hexagonal | Hexagonal | Hexagonal | Hexagonal | Indefinite | Indefinite | Indefinite |

TABLE 1-continued

|  |  | Ex. 1 | Ex. 2 | Ex. 3 | Ex. 4 | Compar. Ex. 1 | Compar. Ex. 2 | Compar. Ex. 3 | Compar. Ex. 4 |
|---|---|---|---|---|---|---|---|---|---|
|  |  | plate shape | plate shape | plate shape | plate shape | plate shape | shape | shape | shape |
|  | Primary particle diameter (μm) | 1.07 | 1.06 | 1.07 | 0.07 | 1.05 | 0.11 | 0.12 | 0.11 |
|  | Aspect ratio | 5.4 | 5.5 | 5.4 | 3.6 | 5.6 | 2.3 | 2.1 | 2.2 |
|  | Zn element amount (Fluorescence X-ray analysis value (%) (on ZnO basis)) | 90.4 | 89.5 | 89.7 | 92.6 | 100 | 100 | 82.4 | 81.1 |
|  | Ti element amount (Fluorescence X-ray analysis value (%) (on $TiO_2$ basis)) | 9.4 | Undetected | 4.9 | Undetected | Undetected | Undetected | 17.4 | Undetected |
|  | Fe element amount (Fluorescence X-ray analysis value (%) (on $Fe_2O_3$ basis)) | Undetected | 10.5 | 5.4 | 7.3 | Undetected | Undetected | Undetected | 18.7 |
| Physical property of coating film | Total light transmittance 1 (%) | 53 | 52 | 53 | 20 | 71 | 45 | 46 | 42 |
|  | Total light transmittance 2 (%) | 54 | 47 | 52 | 17 | 61 | 39 | 45 | 37 |
|  | Ultraviolet shielding ratio 1 (%) | 47 | 48 | 47 | 80 | 29 | 55 | 54 | 58 |
|  | Ultraviolet shielding ratio 2 (%) | 46 | 53 | 48 | 83 | 39 | 61 | 55 | 63 |
|  | Ratio of (Ultraviolet shielding ratio 1 (%) of coating film containing coated zinc oxide particles)/(Ultraviolet shielding ratio 1 (%) of coating film containing the raw zinc oxide particles as the matrix of the coated zinc oxide particles) | 1.6 | 1.7 | 1.6 |  |  |  | 1.0 | 1.0 |
|  | Ratio of (Ultraviolet shielding ratio 2 (%) of coating film containing coated zinc oxide particles)/(Ultraviolet shielding ratio 2 (%) of coating film containing the raw zinc oxide particles as the matrix of the coated zinc oxide particles) | 1.2 | 1.3 | 1.2 |  |  |  | 0.9 | 1.0 |

(Evaluation Method)
(Composition of Obtained Particles)

The X-ray diffraction spectrum shown in FIGS. 2, 4, 6, 8, 12, and 14 and the compositions of the obtained particles in Table 1 show results of performing analysis using an X-ray diffractometer Ultima III (manufactured by Rigaku Corporation) having an X-ray tube with copper.

(Measurement Method of Ultraviolet Shielding Ratio)
(Preparation of Coating Film)

In a mayonnaise bottle having a volume of 75 ml, 2 g of zinc oxide particles in each of examples and comparative examples described above, 10 g of varnish (ACRYDIC A-801-P manufactured by DIC Corporation), 5 g of butyl acetate (special grade reagent, manufactured by Wako Pure Chemical Industries, Ltd.), 5 g of xylene (genuine special grade, manufactured by JUNSEI CHEMICAL CO., LTD.) and 38 g of glass beads (1.5 mm, manufactured by Potters-Ballotini Co., Ltd.) were put and sufficiently mixed, then fixed in a paint conditioner Model 5410 (manufactured by RED DEVIL, Inc.), and subjected to a dispersion treatment by giving vibrations for 90 minutes, thereby preparing a coating. Next, a small amount of the prepared coating was added dropwise onto a slide glass (length/width/thickness=76 mm/26 mm/0.8 to 1.0 mm, manufactured by Matsunami Glass Ind., Ltd.), and a coating film was prepared using a bar coater (No. 579 ROD No. 6, manufactured by YASUDA SEIKI SEISAKUSHO, LTD.). The prepared coating film was dried at 20° C. for 12 hours, and then used for measurement.

Figure 15:
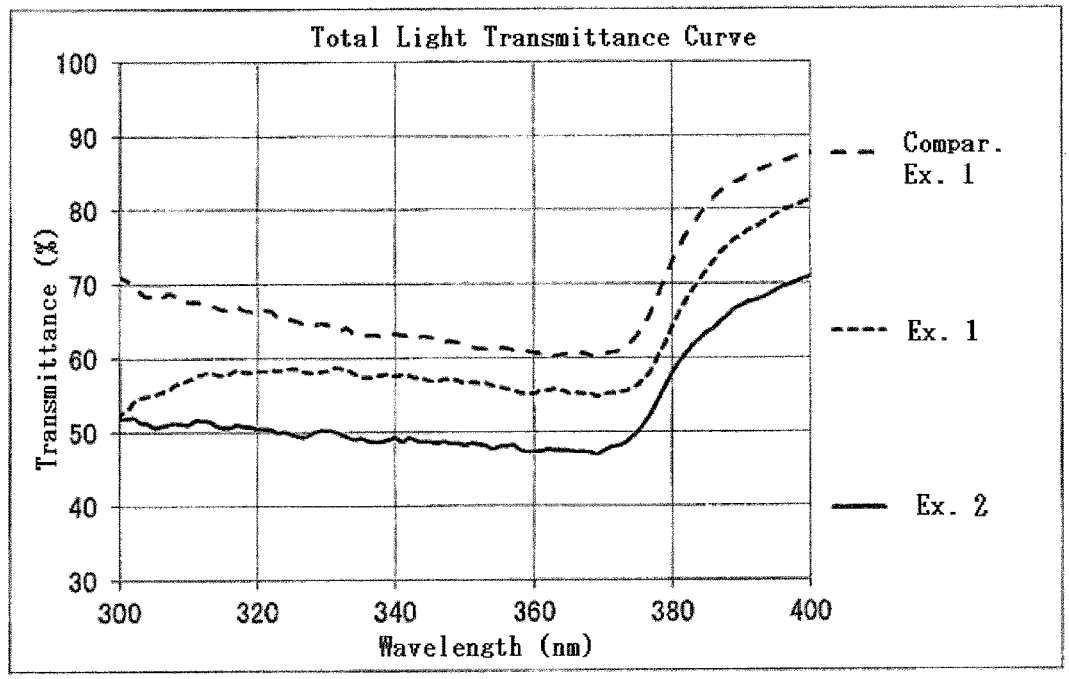
FIG. 15 shows total light transmittance curves in the ultraviolet wavelength region of 300 to 400 nm defined by an ultraviolet shielding ratio of a coating film containing $Zn_2TiO_4$-coated zinc oxide particles of example 1, an ultraviolet shielding ratio of a coating film containing $ZnFe_2O_4$-coated zinc oxide particles of example 2, and an ultraviolet shielding ratio of a coating film containing zinc oxide particles of comparative example 1.

Each coating film was prepared by using the $Zn_2TiO_4$-coated zinc oxide particle of example 1, the $ZnFe_2O_4$-coated zinc oxide particle of example 2, and the zinc oxide particles of comparative example 1 based on the above-mentioned composition, and measured by a spectrophotometer V-570 (manufactured by JASCO Corporation). The results of the total light transmittance curves at the ultralight wavelength region of 300 to 400 nm are shown in FIG. 15. Although the total light transmittance depends on the particle diameter, it was found that the primary particle diameters of the particles of examples 1 and 2, and comparative example 1 are almost the same from table 1.

From the results of FIG. 15, it is clear that the zinc oxide particle of the present disclosure is superior to the conventional hexagonal plate-shaped zinc oxide particle in the ultraviolet shielding performance.

From the results of the ratios of (ultraviolet shielding ratio of a coating film containing the coated zinc oxide particle (o))/(ultraviolet shielding ratio of a coating film containing the raw zinc oxide particle which is the matrix of the coated zinc oxide particle (%)) in Table 1, it is clear that the coated zinc oxide particles of examples 1, 2, and 3 are superior to the raw zinc oxide particle in the ultraviolet shielding property.

Further, the above-mentioned ratios concerning the ultraviolet shielding ratios 1 and 2 of comparative examples 3 and 4 are 1.0 or less, respectively. Therefore, it is clear that the ultraviolet shielding ratio is not always improved by the covering with $Zn_2TiO_4$ and/or $ZnFe_2O_4$. Then, the above-mentioned ratios concerning the coated zinc oxide particles of examples 1, 2, and 3 are 1.2 or more, especially concerning the ultraviolet shielding ratio 1, the ratios are 1.6 or more. Therefore, it is clear that the ultraviolet shielding performance is remarkably improved by the covering specified in the present disclosure.

Further, the ultraviolet shielding ratio is higher as the particle diameter is smaller, but in this case, it is not preferred to use as a cosmetic component because the slippage is reduced. The zinc oxide particle of comparative example 1 has a good slippage derived from the shape and particle diameter, but the ultraviolet shielding ratio is low as shown in table 1. On the other hand, the ultraviolet shielding ratios of the coated zinc oxide particles of comparative examples 3 and 4 are high because of small particle diameter, but a good slippage cannot be obtained.

Each of the coated zinc oxide particles of examples 1, 2, and 3 have a hexagonal plate shape and a particle diameter of about 1 μm so that the slippage thereof is high, further the ultraviolet shielding ratio thereof is higher than the zinc oxide particle of comparative example 1 having almost the same particle diameter and the same shape. That is, it is clear that the coated zinc oxide particles of examples 1, 2, and 3 have a high ultraviolet shielding ratio and suitable slippage. As described before, the zinc oxide particle of the present disclosure is superior zinc oxide particle having a high slippage, a soft focus effect, and a high ultraviolet shielding ratio.

INDUSTRIAL APPLICABILITY

The zinc oxide particle of the present disclosure can be used as a component of a cosmetic, an ink, a coating, and so on.

The invention claimed is:

1. A coated zinc oxide particle comprising a zinc oxide particle and a layer covering a surface of the zinc oxide particle,
wherein the zinc oxide particle has a hexagonal plate shape with an aspect ratio of 2.5 or more and a primary particle diameter of 0.01 μm to 100 μm, and
the layer is formed essentially of $Zn_2TiO_4$ and/or $ZnFe_2O_4$.

2. The coated zinc oxide particle according to claim 1, wherein an amount of a Ti element and/or a Fe element is 5 wt % or more and 30 wt % or less relative to 100 wt % of the zinc oxide particle in terms of $TiO_2$ and/or $Fe_2O_3$.

3. A method for producing the coated zinc oxide particle according to claim 1, comprising a step (1-1) of adding an aqueous solution of a titanium salt and/or an iron salt and an alkaline aqueous solution to a water-based slurry of raw zinc oxide particles having a hexagonal plate shape at a temperature of 10° C. to 90° C. while keeping a pH at 9±3, and a step (1-2) of baking the coated zinc oxide particle obtained in the step (1-1).

4. A method for producing the coated zinc oxide particle according to claim 1, comprising a step (2-1) of adding raw zinc oxide particles to an aqueous solution of a zinc salt obtained by dissolving a titanium salt and/or an iron salt and heat aging the raw zinc oxide particles, and a step (2-2) of baking the titanium hydroxide-containing zinc oxide particle and/or iron hydroxide-containing zinc oxide particle obtained in the step (2-1).

5. A coated zinc oxide particle obtained by the method according to claim 3.

6. An ultraviolet shielding agent comprising the coated zinc oxide particle according to claim 1.

7. A cosmetic comprising the coated zinc oxide particle according to claim 1.

* * * * *